US 7,481,777 B2

(12) United States Patent
Chan et al.

(10) Patent No.: US 7,481,777 B2
(45) Date of Patent: Jan. 27, 2009

(54) LANCET INTEGRATED TEST ELEMENT TAPE DISPENSER

(75) Inventors: Frank A. Chan, Sunnyvale, CA (US); Daniel Wong, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 173 days.

(21) Appl. No.: 11/326,422

(22) Filed: Jan. 5, 2006

(65) Prior Publication Data

US 2007/0173740 A1 Jul. 26, 2007

(51) Int. Cl.
*A61B 5/00* (2006.01)
*C12Q 1/00* (2006.01)

(52) U.S. Cl. ............... 600/583; 600/181; 600/182; 600/183; 422/22

(58) Field of Classification Search ............ 600/583, 600/584; 422/66; 606/181–183
See application file for complete search history.

(56) References Cited

U.S. PATENT DOCUMENTS

| | | | |
|---|---|---|---|
| 3,526,480 A | 9/1970 | Findi et al. | |
| 3,620,678 A | 11/1971 | Guigan et al. | |
| 3,786,510 A | 1/1974 | Hodges | |
| 4,218,421 A | 8/1980 | Mack, Jr. et al. | |
| 4,328,184 A | 5/1982 | Kondo | |
| 4,878,971 A * | 11/1989 | Tsunekawa et al. | 156/70 |
| 4,883,642 A | 11/1989 | Bisconte | |
| 4,995,402 A | 2/1991 | Smith et al. | |
| 5,047,044 A | 9/1991 | Smith et al. | |
| 5,077,010 A | 12/1991 | Ishizaka et al. | |
| 5,096,828 A | 3/1992 | Ishizaka et al. | |
| 5,152,775 A * | 10/1992 | Ruppert | 606/182 |
| 5,178,835 A | 1/1993 | Uekusa et al. | |
| 5,228,972 A | 7/1993 | Osaka et al. | |
| 5,679,311 A | 10/1997 | Harttig et al. | |
| 5,686,829 A | 11/1997 | Girault | |
| 5,997,817 A | 12/1999 | Crismore et al. | |
| 6,488,891 B2 | 12/2002 | Mason et al. | |

(Continued)

FOREIGN PATENT DOCUMENTS

DE 198 19 407 A1 11/1999

(Continued)

OTHER PUBLICATIONS

International Patent Application PCT/EP2007/00018 Partial Search Report mailed May 7, 2007.

(Continued)

*Primary Examiner*—Max Hindenburg
*Assistant Examiner*—Michael C Stout
(74) *Attorney, Agent, or Firm*—Woodard, Emhardt, Moriarty, McNett & Henry LLP

(57) ABSTRACT

A lancet integrated test element tape includes a plurality of lancet integrated test elements. The lancet integrated test elements each include a lancet configured to form an incision in tissue and a test element configured to analyze body fluid from the incision in the tissue. A cartridge includes a supply compartment configured to store an unused section of the tape. The tape is folded within the supply compartment to limit damage to the lancet integrated test elements. The cartridge can further include a waste compartment in which a used section of the tape is stored. An indexing mechanism moves the tape between the supply and waste compartments.

16 Claims, 10 Drawing Sheets

U.S. PATENT DOCUMENTS

| | | | |
|---|---|---|---|
| 6,712,253 B2 * | 3/2004 | Hargrave et al. | 225/100 |
| 6,887,709 B2 | 5/2005 | Leong | |
| 7,299,081 B2 | 11/2007 | Mace et al. | |
| 2002/0052618 A1 | 5/2002 | Haar et al. | |
| 2002/0076349 A1 | 6/2002 | Aitken et al. | |
| 2002/0076357 A1 | 6/2002 | Hahs et al. | |
| 2002/0169411 A1 | 11/2002 | Sherman et al. | |
| 2002/0188224 A1 * | 12/2002 | Roe et al. | 600/584 |
| 2003/0050573 A1 | 3/2003 | Kuhr et al. | |
| 2003/0083685 A1 | 5/2003 | Freeman et al. | |
| 2003/0146654 A1 * | 8/2003 | Nguyen et al. | 297/463.2 |
| 2003/0199789 A1 | 10/2003 | Boecker et al. | |
| 2003/0211619 A1 * | 11/2003 | Olson et al. | 436/44 |
| 2003/0233113 A1 * | 12/2003 | Alden et al. | 606/182 |
| 2004/0108046 A1 * | 6/2004 | Kerr et al. | 156/204 |
| 2004/0120848 A1 * | 6/2004 | Teodorczyk | 422/22 |
| 2004/0134809 A1 * | 7/2004 | Urano | 206/312 |
| 2004/0138688 A1 * | 7/2004 | Giraud | 606/181 |
| 2004/0249311 A1 * | 12/2004 | Haar et al. | 600/584 |
| 2004/0251264 A1 * | 12/2004 | Brinkmann | 221/31 |
| 2005/0232815 A1 | 10/2005 | Ruhi et al. | |
| 2005/0245954 A1 * | 11/2005 | Roe et al. | 606/181 |
| 2006/0234388 A1 | 10/2006 | Wong et al. | |
| 2007/0207910 A1 * | 9/2007 | Neubauer et al. | 493/434 |

FOREIGN PATENT DOCUMENTS

| | | |
|---|---|---|
| DE | 198 49 539 S1 | 5/2000 |
| DE | 198 57 426 A1 | 6/2000 |
| EP | 0 637 749 A2 | 2/1995 |
| EP | 1 203 563 A2 | 5/2002 |
| EP | 1 321 769 A1 | 6/2003 |
| JP | 1105157 A1 | 4/1989 |
| JP | 05-010951 | 1/1993 |
| JP | 5045363 A1 | 2/1993 |
| WO | WO 93/09710 A1 | 5/1993 |
| WO | WO 1998/14125 | 4/1998 |
| WO | WO 02/18940 A2 | 3/2002 |
| WO | WO 2004/060174 A2 | 7/2004 |
| WO | WO2005/04948 A1 | 11/2005 |
| WO | WO 2006/092281 A2 | 9/2006 |

OTHER PUBLICATIONS

U.S. Appl. No. 11/070,502, filed Mar. 2, 2005, Roe.

Calasso et al., U.S. Appl. No 11/537,791 entitled "Test Magazine and Method for Processing the Same". filed Oct. 2, 2006.

* cited by examiner

LANCET INTEGRATED TEST ELEMENT TAPE DISPENSER

BACKGROUND

The present invention generally relates to bodily fluid sampling devices and more specifically, but not exclusively, concerns a dispenser for lancet integrated test element units that is configured to minimize the risk of damage of the units prior to use.

The acquisition and testing of bodily fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various bodily fluids, and for certain applications, is particularly related to the testing of blood and/or interstitial fluid. Performing home-based testing can be difficult for many patients, especially for patients with limited hand dexterity, such as the elderly or diabetics. For example, diabetics can sometimes experience numbness or tingling in their extremities, such as their hands, which can make self-testing difficult because they are unable to accurately position a test strip to collect the blood sample. In addition, wounds for diabetics tend to heal more slowly, and as a result, there is a desire to make incisions less invasive.

Recently, lancet integrated test strips or elements have been developed in which a test strip is integrated with a lancet or other piercing means so as to form a single disposable unit. While these integrated units have somewhat simplified the collection and testing of fluid samples, there are still a number of issues that need to be resolved before a commercial unit can be implemented. One issue concerns maintaining the sterility of the lancet prior to use so as to minimize the risk of infection. Another issue concerns the disposal of used units after use. Once used, the integrated units become a biohazard that need to be disposed of in a safe manner. A number of different types of systems have been proposed for dispensing test strips, lancets, or some combination thereof, but most of these systems have significant drawbacks, especially when used in conjunction with integrated units.

In one typical design, individual test strips are stacked within a cartridge. The test strips are usually dispensed on an individual basis either manually or via a sliding mechanism. Since test strips are dispensed individually, automatic handling of the test strips is rather complicated. The sliding mechanism can jam during dispensing, which can damage the test strips. Usually, after use, the test strips have to be disposed of manually via a separate waste container.

Individual test strips or elements have been formed and/or connected together to form tapes of test strips. In one design, the tape is folded within a case, and individual test elements are manually dispensed by pulling on the tape. However, in the age of smaller fluid sample sizes in which the size of test strips becomes smaller, manual feeding and handling of the tape is not practical due to the size of the test strips involved. Such manual feed designs also fail to provide for automatic feeding of the tape and automatic disposal of used sections of the tape, which are typically needed for modern systems. To address these concerns, automatic feed systems like reel-to-reel cassettes have been developed.

Reel-to-reel type cassettes of test strips, which are similar in construction to normal audio cassettes, address a number of test strip handling and storage issues found with previous test strip cartridge designs. However, it has been recognized that there are still a number of significant drawbacks to reel-to-reel type cassettes, especially for electrochemical test strips, lancet integrated test strips, and other disposables that contain components susceptible to damage. For example, if electrochemical test strips are tightly wound around a reel in the cassette, the electrodes within the test strip can be bent or damaged in such a way to create a short, an open condition, or otherwise damage the electrodes, thereby making the test strip unusable. Similarly, if tightly wound around a reel, lancets within integrated units can be bent or otherwise damaged, which in turn can cause injury to the user or otherwise prevent successful lancing of the skin. To combat this problem, tapes of test strips or integrated units are loosely wound around the reels. However, the loosely wound tape makes the cassettes larger than desired and/or reduces the number of tests available before requiring reloading a new cassette. Even when the tape is initially wrapped in a loose manner, the tape can become tightly wrapped as the tape is indexed, thereby damaging the tape. In addition, reel-to-reel type cassette designs are prone to operating in reverse, which can cause the reintroduction of used test strips into the sterilized supply compartments.

Thus, needs remain for further contributions in this area of technology.

SUMMARY

One aspect concerns a lancet integrated test tape that includes a plurality of lancet integrated test units. The lancet integrated test units each include a lancet configured to form an incision in tissue and a test element configured to analyze body fluid from the incision in the tissue. A cartridge includes a supply compartment configured to store an unused section of the tape. The tape is folded within the supply compartment to limit damage to the lancet integrated test units.

Another aspect concerns a tape that includes a plurality of test elements configured to analyze body fluid. A cartridge includes a supply compartment configured to store an unused section of the tape. The unused section of the tape is folded within the supply compartment. The cartridge further includes a waste compartment configured to store a used section of the tape. An indexing mechanism is configured to index the tape between the supply compartment and the waste compartment.

A further aspect concerns a tape that includes a plurality of test elements configured to analyze body fluid. A cartridge includes a supply compartment configured to store an unused section of the tape. The unused section of the tape is folded within the supply compartment. The cartridge further includes a waste compartment configured to store a used section of the tape. The used section of the tape is folded within the waste compartment.

Still yet another aspect concerns a technique in which a plurality of test elements are configured to analyze body fluid are assembled on a sterility sheet. A plurality of piercing members configured to pierce tissue are enclosed in the sterility sheet. Each piercing member is associated with one of the test elements to create a tape of integrated sampling elements.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
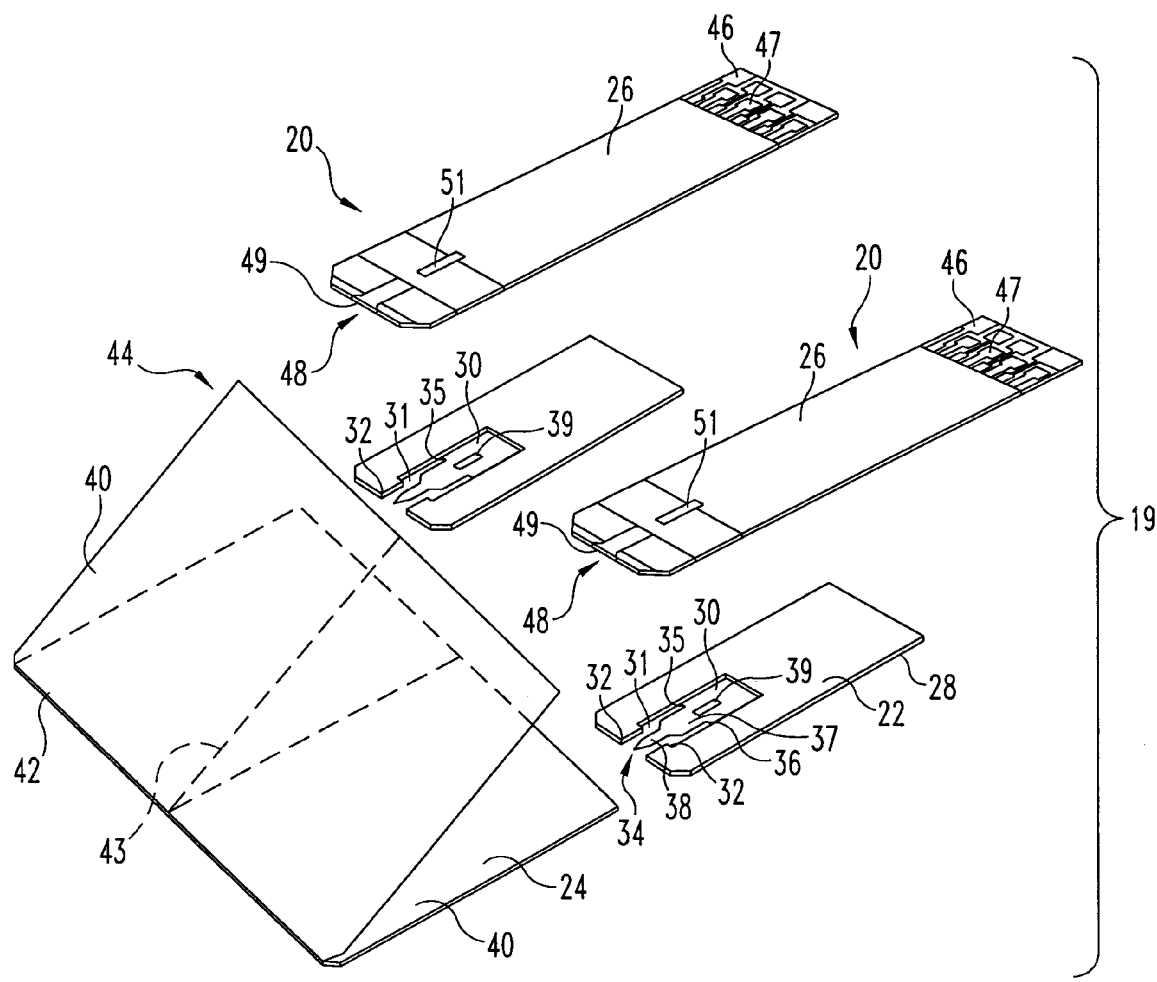
FIG. 1 is an exploded view of a lancet integrated test element tape according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. A number of embodiments of the invention are shown in detail; although it will be apparent to those skilled in the relevant art that some features that are not relevant to the present invention may not be shown for the sake of clarity. It should be noted that directional terms, such as "up", "down", "top" and "bottom", are used herein solely for the convenience of the reader in order to aid in the reader's understanding of the illustrated embodiments, and it is not the intent that the use of these directional terms in any manner limit the described, illustrated, and/or claimed features to a specific direction or orientation.

As mentioned previously, there have been a number of drawbacks prior cartridge or cassette designs. For example, tapes of lancets, test strip and/or lancet integrated test element (LIT) units can be damaged if tightly wound around a supply reel of a reel-to-reel cassette or other cassette types. To address these issues as well as other concerns, a LIT tape according to one embodiment is stored in a folded manner within a supply compartment. By being stored in a folded manner, the tension applied to the tape during indexing is typically applied to only a few of the LIT units, which in turn reduces the chance of the LIT units being damaged. To further reduce the chance of damaging the LIT units, a feed mechanism can be used to automatically feed the tape between the supply and waste compartments of the cartridge. The feed mechanism allows the LIT units to be positioned properly for lancing and sample collection without the need for any user manipulation.

A LIT tape 19 according to one embodiment, among many, will be described initially with reference to FIG. 1. Referring to FIG. 1, the tape 19 includes multiple LIT devices or units 20. For further information regarding the individual units 20, reference is made to U.S. patent application Ser. No. 11/070,502, filed Mar. 2, 2005, currently pending, which is incorporated by reference in its entirety. Each unit 20 includes a lancet assembly or incision forming member 22 for forming an incision in tissue, a sterility sheet 24 for maintaining the sterility of the lancet assembly 22 as well as connecting the units 20 together, and a test strip 26 for acquiring a body fluid from the incision. In the illustrated embodiment, the incision forming member 22 will described with reference to a lancet. It should be recognized that the lancet 22 can include other devices that puncture, cut, pierce, and/or otherwise ruptures tissue, like needles and blades, to name a few examples. Both the lancet 22 and the test strip or element 26 in the illustrated embodiment are generally flat such that the integrated lancing test strip 20 has an overall flat appearance. Although the common term "test strip" has been used to aid the reader in understanding the below described embodiments, it should be noted that the test elements or other biosensors described herein should not be limited to those shaped in the form of a strip, but rather, the test elements can be shaped differently. By being flat, multiple units 20 can be folded in compact manner inside a cartridge, which allows a plurality of units 20 to be used without the need to individually load and/or dispose of used units 20. Furthermore, the overall flat shape allows the LIT tape 19 to be manufactured with a continuous process in which layers of component materials can be layered to form contiguous strips of units 20. It should nonetheless be recognized that the LIT tape 19 and/or the LIT units 20 in other embodiments can have a different overall shape.

As can be seen in FIG. 1, the lancet assembly 22 has a retainer or guide member 28 that guides a piercing member or lancet 30 during lancing. The lancet 30 is slidably retained within a guide slot or opening 31 that is defined in a retainer 28. In the course of lancing, the guide slot 31 guides the movement of the lancet 30 during both extension and retraction. In the illustrated embodiment, the lancet 30 and the retainer 28 are separate components that are not directly attached to one another. Nevertheless, in other embodiments, the lancet 30 and the retainer 28 can be connected to one another. For example, the lancet assembly 22 can have breakable tabs that connect the lancet 30 to the retainer 28 so that the lancet 30 is held in place during manufacturing as well as prior to lancing, thereby reducing the risk of injury. During lancing, the tabs are broken to allow the lancet 30 to extend from the integrated lancing test strip 20. In another example, a spring for retracting the lancet 30 connects the retainer 28 to the lancet 30.

As shown, end stops 32 of the retainer 28 extend inwardly at a slot opening 34 of the guide slot 31 so as to limit the movement of the lancet 30, thereby retaining the lancet 30 in the guide slot 31. The lancet 30 has a body portion 35 with one or more stop edges 36, which are wider than the slot opening 34. When the lancet 30 is fully extended, the stop edges 36 of the lancet 30 can contact the end stops 32, and thus, limit the travel of the lancet 30. However, in other embodiments, the firing mechanism, which is used to fire the lancet 30, limits the travel of the lancet 30. A neck portion 37 of the lancet 30, which is slightly smaller that the size of the slot opening 34, extends from the body portion 35 of the lancet 30. During extension of the lancet 30, the neck 37 is received between the end stops 32 such that the end stops 32 can limit undesirable rotation of the lancet 30 as the tissue is punctured. Extending from the neck 37, the lancet 30 has a blade portion or tip 38 that is configured to cut tissue. In the illustrated embodiment, the lancet defines an engagement notch 39 for coupling the lancet 30 to a firing mechanism. In one form, the lancet assembly 22 is made at least in part of medical grade stainless steel, but it should be recognized that the lancet assembly 22 can be made of other materials, such as ceramics and/or plastics. Furthermore, it is contemplated that the guide member 28 and the lancet 30 can be made of different materials and/or manufactured separately. In one embodiment, the guide member 28 and lancet 30 are formed by a photo-etching technique in which a sheet of metal is photo-etched to form both the guide member 28 and the lancet 30, and in another embodiment, the lancet assembly 22 is manufactured via stamping. The lancet assembly 22 in still other embodiments can be manufactured through other techniques as would occur to those skilled in the art.

With reference to FIGS. 1, after the lancet assembly 22 is formed, the lancet assembly 22 can be then packaged within the sterility sheet 24. As will be appreciated from the discussion below, the lancet assembly 22 can be packaged in the sterility sheet 24 before, during, or after the lancet assembly 22 is sterilized. In the illustrated embodiment, the sterility sheet 24 is a sheet of metallic foil, and in another embodiment, the sterility sheet 24 is made of plastic. It should be recognized that the sterility sheet 24 can be made of other types of materials. During manufacturing, the sterility sheet 24 is folded into two flaps 40 with a crease or fold 42 in between, as is shown in FIG. 1. After folding, the lancet assemblies 22 are sandwiched between the two folds 40 such that the crease 42 closes the slot opening 34 of the guide slot 31 in the lancet assembly 22. The flaps 40 are secured to the opposite (flat) sides of the lancet assembly 22 so that the lancet 30 is sealed inside the guide slot 31 with the slot opening 34 closed by the crease 42. In one form, an adhesive is used to secure the sterility sheet to the guide member 28. Adhesive is applied on the guide member 28 around the guide slot 31, but is not applied to the lancet 30 so that the lancet 30 is able to still slide within the guide slot 31. Although an adhesive is used in the illustrated embodiment, it should be understood that the sterility sheet 24 can be sealed with the guide member 28 in other manners, such as through heat sealing. In the illustrated embodiment, the edges of the flaps 40 are not sealed together, but it is envisioned that in other embodiments the edges of the sterility sheet 24 can be sealed together so as to form a pocket that encloses the entire lancet assembly 22. In still yet another embodiment, instead of folding the sterility sheet 24, two sterility sheets 24 are joined together with the lancet assembly 22 sandwiched in between.

As depicted, the integrated lancing test strips 20 in one embodiment are formed in a continuous process. In the continuous process, the sterility sheet 24 is a continuous band that is rolled off a reel and folded around a continuous band or belt of lancet assemblies 22 that are likewise rolled from a reel. The lancet assemblies 22 are sealed between the flaps 40 of the sterility sheet 24 and the test elements 26 are attached to the sheet 24 in the manner as described above. The sterility sheet 24 joins adjacent LIT units 20 together to form the continuous LIT tape 19. Between the individual units 20, the sterility sheet 24 has folds or weakened lines 43 that allow the tape 19 to be folded in a fan-fold fashion for storage. The fold lines 43 can also be configured to allow individual units 20 to be detached from one another. The sterility sheet 24 can be weakened at the fold lines 43 in any number of manners as would occur to those skilled in the art. For example, the sheet 24 can be scored or thinned at the fold line 43, and it is contemplated that the fold line 43 can be continuous or discontinuous. The fold lines 43 can be formed before the lancet assembly 22 is covered by the sterility sheet 24 or afterwards. It is envisioned that the fold line 43 in other embodiments can be optional such that the tape 19 naturally folds in a fan-fold or other fashion.

Once joined together, the lancet assembly 22 and the sterility sheet 24 form a lancet package or packet 44. As mentioned before, the lancet assembly 22 can be sterilized before being enclosed in the sterility sheet 24 or afterwards. The lancet assembly 22 can be sterilized through any number of sterilization techniques as would occur to those skilled in the art, such as through chemical, heat, and/or radiation sterilization techniques, to name a few. It should be understood that all or part of the lancet assembly 22 can be sterilized. For instance, only the lancet 30 and guide slot 31 can be sterilized, if so desired. In another embodiment, the lancet assembly 22 is sterilized after the lancet assembly 22 is packaged inside the lancet package 44. In one form, a radiation sterilization technique is used once the lancet 30 is enclosed by the sterility sheet 24. With the lancet package 44, sterilization of the lancet assembly 22 can occur without exposing the test strip 26 to the undesirable affects of lancet sterilization. Consequently, the lot specific calibration data can be generated before the lancet package 44 is attached to the test strip.

In the illustrated embodiment, the test strip 26 is an electrochemical type test strip. In one particular form, the test strip 26 includes a modified version of any of the ACCU-CHEK® brand test strips (Roche Diagnostics GmbH), but it is envisioned that other types of test elements can be used. For example, the test strip 26 in other embodiments can include an optical type test strip or can analyze fluid samples in other manners. At one end, the test strip 26 in the illustrated embodiment includes a connection portion 46 with electrical contacts 47 that transmit sample readings to a meter. Opposite the connection portion 46, the test strip 26 has a capillary channel 48 with a capillary opening 49 that is configured to draw a body fluid sample from an incision formed by the lancet 30 via capillary action. As should be appreciated, the test strip 26 inside the capillary channel 48 includes an analysis region that includes electrodes, such as working, counter and reference electrodes, and reagents for analyzing the fluid sample. In one form, the connection portion 46 is connected to a meter, and the sample readings from the electrodes in the analysis region are transmitted to the meter via the electrical contacts.

As briefly noted before, the sterilized lancet package 44 is attached to the test strip 26 to form the integrated lancing test strip unit 20. As depicted, the lancet package 44 is attached at the end of the test strip 26 proximal to the capillary opening 49 of the capillary channel 48. In particular, the guide slot opening 34 of the lancet assembly 22 and the capillary opening 49 of the test strip 26 are positioned near one another in a side-by-side relationship so that when the lancet 30 forms the incision, the capillary channel opening 49 is positioned in close proximity to collect the body fluid. The test strip 26 is attached to the exterior of the sterility sheet 24 enclosing the lancing member 22 to complete the integrated test strip 20. The test strip 26 in one form is attached to the lancet package 44 through an adhesive, but it should be recognized that the test strip 26 and lancet package 44 can be attached in other manners. In one form, the lancet package 44 is attached to the test strip 26 such that the end edges of both are aligned with another. However, in other embodiments the edges of the lancet package 44 and the test strip 26 can be offset from one another. For example, the edge of the lancet package 44 in the illustrated embodiment, as is demarked by crease 42, is recessed slightly from the edge of the test strip 26 at the capillary opening 49. By having the lancet package 44 recessed, fluid flow to the capillary channel opening 49 is promoted. In another example, the sterility sheet 24 is positioned such that the crease 42 extends past the edge of the test strip 26. With this example, all or part of the sterility sheet 24 can be hydrophobic and/or hydrophilic so as to direct fluid flow towards the capillary channel 48. In one particular form, the sterility sheet 24 extends from the test strip 26 such that the sterility sheet 24 acts like a flexible wicking flag that draws fluid into the capillary channel 48.

To draw the body fluid towards the capillary channel opening 49 and away from the lancet 30, the test strip 26 in the illustrated embodiment has a fluid direction notch facing the lancet package 44. In order to enhance fluid flow towards the capillary channel opening 49, the sterility sheet 24 can be treated and/or made to be hydrophobic. With the sterility sheet 24 being hydrophobic, the sterility sheet can squeegee or wipe body fluid from the lancet 30 as the lancet 30 retracts back inside the guide slot 31. It is thought that the wiping action of the sterility sheet 24 increases the amount of body fluid available for sampling as well as makes the lancet 30 cleaner for disposal purposes. As noted before, with the lancet 30 sealed in the lancet package 44, the risk of cross-contamination between the lancet 30 and the test strip 26 is reduced.

In FIG. 1, the test strip 26 further defines a relief slot 51 through which a blade tip of a cam arm extends when engaging the lancet 30 during loading and firing. In addition, the relief slot 51 can be used to vent air from the capillary channel 48 as fluid is collected. The length of the relief slot 51 generally approximates the length of the lancing stroke of the firing mechanism used to actuate the lancet 30. When the lancet package 44 is attached to the test strip 26, the engagement notch 39 on the lancet 30 is aligned with the relief slot 51 in the test strip 26. As is described in greater detail in U.S. patent application Ser. No. 11/070,502, filed Mar. 2, 2005, which is again incorporated by reference in its entirety, the blade tip of a cam arm for the firing mechanism extends through the engagement notch 39 of the lancet 30 as well as into the relief slot 51. When doing so, the blade tip pierces the sterility sheet 24. During lancing, the cam arm via the blade extends and retracts the lancet 30 relative to the test strip 26. As the lancet 30 extends, the tip 38 of the lancet 30 pierces the sterility sheet 24 at crease 42. In one form, the sterility sheet 24 at the crease 42 is weakened so as to aid in puncturing by the lancet 30, but in other forms, the crease 42 is not weakened. Once the lancet 30 is retracted back inside the guide slot 31, the two flaps 40 of the sterility sheet 24 can hold the lancet 30 inside through friction. By engaging the lancet 30 in such a manner, the risk of accidental puncturing by the integrated lancing test strip 22 is reduced because it is more difficult to manually and/or accidentally actuate the lancet 30. It should be recognized that the lancet assembly 22 can incorporate other structures for engaging the lancet 30. For instance, the engagement notch 39 in the lancet 30 can be replaced with a protrusion or knob. It is also contemplated that the lancet can be fired through non-mechanical and/or non-contact techniques, which do not require the puncturing of the sterility sheet 24. As an example, the lancet 30 in another embodiment is magnetized and fired magnetically through a voice coil driver or other magnetic drivers. With the lancet 30 enclosed in the sterility sheet 24 both before and after lancing, the risk of contamination is reduced, and the risk of accidental injury is likewise reduced.

Figure 2:
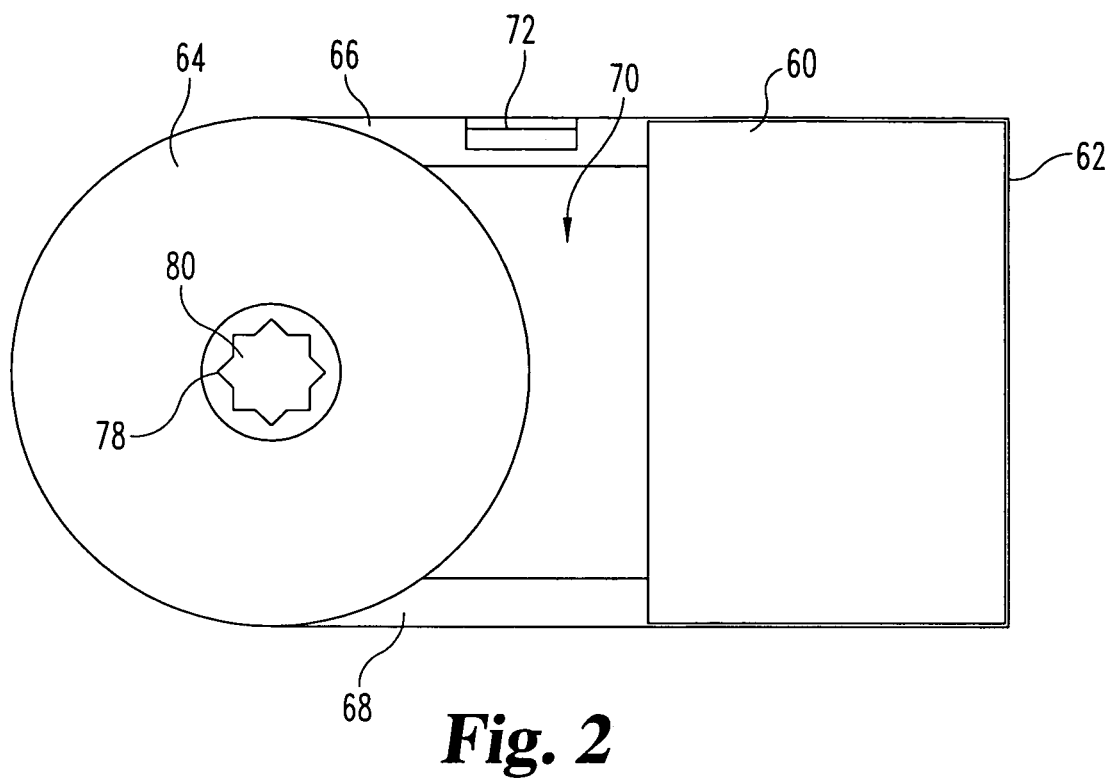
FIG. 2 is a bottom view a cartridge that houses the FIG. 1 test element tape.
Figure 3:
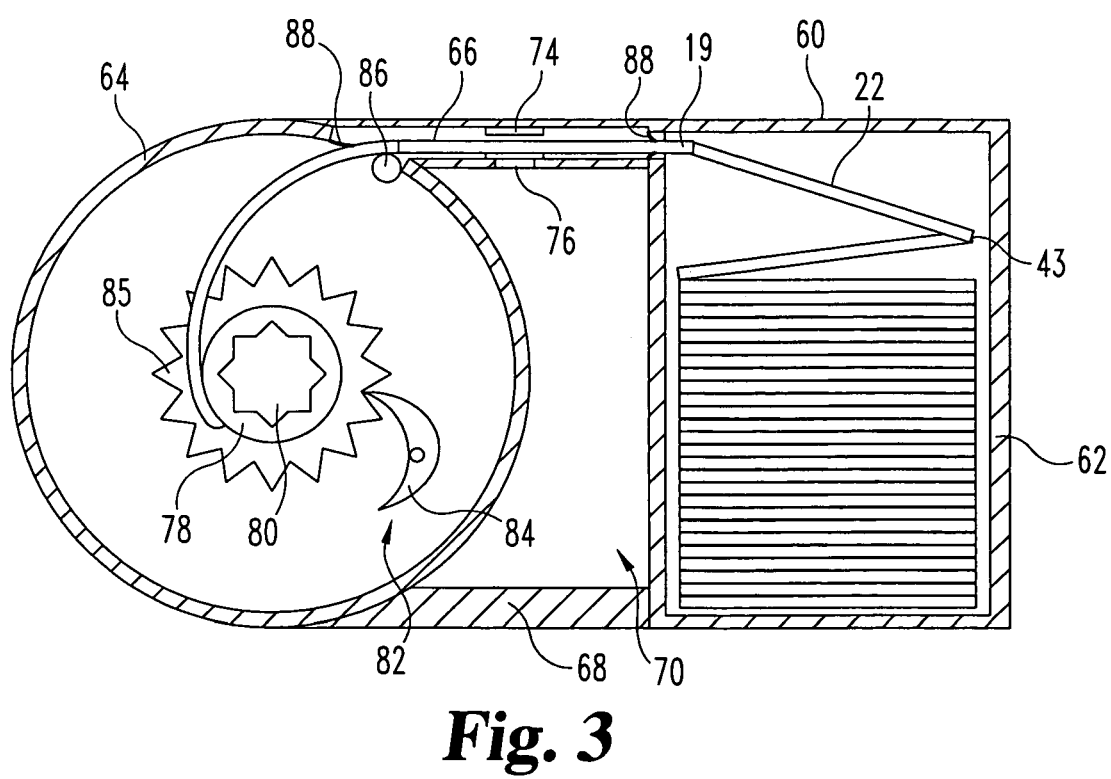
FIG. 3 is a partial, cross-sectional view of the FIG. 2 cartridge.

A cartridge or cassette 60 in which the test element tape 19 is housed in illustrated in FIGS. 2 and 3. FIG. 2 illustrates a top view of the cartridge 60, and FIG. 3 depicts a partial, cross-sectional view of the cartridge 60. As shown, the cartridge 60 includes a supply compartment 62 in which unused LIT units 20 are stored and a waste compartment 64 in which used units 20 are stored. Of note, the LIT units 20 on the tape 19 are folded in a fanfold fashion along fold lines 43 within the supply compartment 62. As noted previously, LITs and test strips can be damaged when wrapped around a reel in cassettes. For example, the lancet in a LIT can be bent or the electrodes, capillary channel, and/or chemistry within the test strip can be damaged when tightly wrapped around a reel in a reel-to-reel type cassette. To avoid damage, the tape is typically wrapped in a loose manner within a reel-to-reel cassette, which tends to waste space. Even when loosely wrapped, the lancet and/or test strip can be bent or otherwise damaged. As the tape is indexed in a reel-to-reel cassette, the tape around the supply reel can tighten, which in turn can damage the components of the tape.

In contrast, the tape 19 in FIG. 3 is folded along the fold lines 43 within the Is supply compartment, which in turn alleviates a number of issues. When folded, the tape 19 in one form may have a crease at the fold lines 43 or may not have a crease in other forms. With the tape 19 folded along the fold lines 43, the individual LIT units 20 remain generally flat or straight, which minimizes the risk of damage. Moreover, when the tape 19 is folded, the LIT units 20 can be tightly packed within the supply compartment 62 without damaging the LIT units 20. Further, the tape 19 can be indexed without causing significant damage to the LIT units in the folded supply tape 19, because the pulling force for indexing is usually applied to merely a few of the LIT units 20 that are about to be used. In the illustrated embodiment, the tape 19 is folded in an alternating fanfold manner, but it should be recognized that the tape 19 can be folded in other manners. For instance, the tape 19 can be folded in an accordion fashion, and/or in another embodiment, the tape 19 includes blank sections between the fold lines 43, which do not include LIT units 20.

Between the supply compartment 62 and the waste compartment 64, the cartridge 60 has a sampling portion 66 where the LIT units 20 sample body fluid and a stabilizer arm 68 that stabilizes the connection between the compartments 62, 64. The sampling portion 66 and/or stabilizer arm 68 can be optional or eliminated in other embodiments. As depicted, the sampling portion 66 and the stabilizer arm 68 define a meter cavity 70 in which at least a portion of the meter is received. In one embodiment, the firing cam arm of the meter, which is configured to engage the engagement notch 39 in the lancet 30 during lancing, extends within the meter cavity. In the embodiment depicted, the sampling portion 66 is generally enclosed to assist in maintaining the sterility of the cartridge 60, but the sampling portion 66 still incorporates a number openings that are used to engage the LIT unit 20 during sampling. Referring to FIG. 2, the sampling portion 66 near the top of the cartridge 60, which faces the meter once engaged, has a contact opening 72 where the contacts of the meter engage the contacts 47 on the LIT units 20. At the bottom of the cartridge 60 that contacts or faces the tissue during fluid acquisition, the sampling portion 66 of the cartridge 60 has a sample opening 74 through which the lancet 30 extends during lancing and the test strip 26 collects fluid during sampling. Near the sample opening 74 the cartridge and/or the meter can incorporate various surfaces (or mechanisms) constructed to express fluid and/or direct the flow of the fluid. Facing the meter opening 70, the sampling portion 66 of the cartridge 60 has a lancet engagement cavity 76 through which the firing arm of the meter engages the engagement notch 39 in the lancet 30. It is envisioned that the sampling portion 66 can be configured in other manners or can be eliminated altogether. For instance, the tape 19 can be exposed to the outside environment when in the sampling portion 66. In another example, the compartments 62, 64 are not directly connected together so that the tape 19 is threaded through the meter in a fashion similar to a film projector.

With reference to FIGS. 2 and 3, the waste compartment 64 includes a take-up reel around which the used section of the tape 19 is wrapped. As shown, the reel defines an engagement socket 80 where the meter engages and rotates the reel 78. As should be appreciated, the reel in other embodiments can be engaged in other manners. With the reel 78, the units 20 on the tape 19 are able to be advanced from the storage compartment 62 to a sampling position, and then once used, the used LIT units 20 are stored in the waste compartment 64. Once the LIT units 20 are used, the tape 19 can be wrapped tightly around the reel 78 without the worry of the resulting damage. Bending of the LIT units 20 will usually damage the units 20, thereby preventing the LIT units 20 from being accidentally used again. Moreover, the bend in the tape 19 reduces the chance of used tape being reinserted into the supply compartment 62, which could potentially contaminate the supply compartment 62. To further reduce the risk of contamination, the cartridge 60 includes a ratchet mechanism 82. As shown in FIG. 3, the ratchet mechanism 82 includes a pawl 84 that engages a gear 85. The pawl 84 can be biased by a spring or other biasing devices. With such a construction, the ratchet mechanism 82 only allows the reel 78 to rotate in one direction such that the tape 19 is only able to travel inside the waste compartment 64. It should be recognized that other types of ratchet mechanisms can be used. The waste compartment 64 further incorporates a guide spindle 86 that guides the tape 19 into the waste compartment 64. To minimize the risk of contamination, the entrances of the compartments 62, 64 include seals 88 that seal against opposite sides of the tape 19. In selected embodiments, the supply compartment 62 includes a desiccant to reduce humidity in the supply compartment 62.

Figure 4:
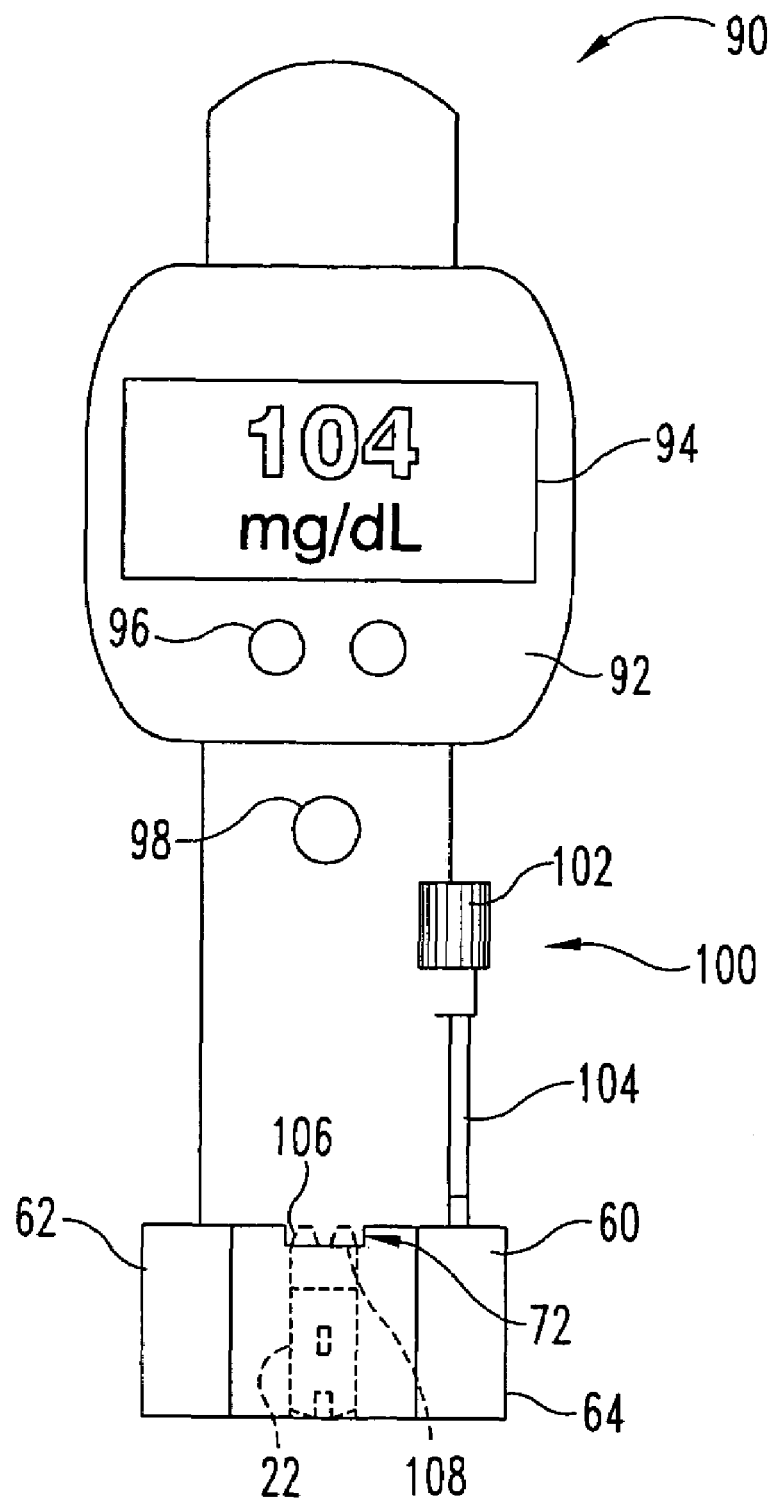
FIG. 4 is a front view of a meter coupled to the FIG. 2 cartridge.

FIG. 4 depicts a body fluid sampling system 90 in which the cartridge 60 is coupled to a meter 92. The cartridge 60 can be coupled to the meter 92 in any number of different manners as would occur to those skilled in the art, such as through a snap fit connection and/or through a bayonet style connection. It is envisioned that in other embodiments the cartridge 60 and meter 92 can be integrated together to form a single unit. Alternatively, the cartridge 60 and meter 92 can be completely separate, but can remotely communicate via a wireless connection or other remote connection. As depicted, the meter 92 includes a display 94 for displaying test results and other information. The meter 92 further includes one or more input buttons 96 for entering information into the meter 92 and a firing button 98 for firing the lancet 30 in the LIT unit 20. The meter 92 can include any number of firing mechanisms for firing the lancet 30 as would occur to those skilled in the art, such as a spring loaded firing mechanism, a voice coil driver and/or an electric motor. As should be appreciated, the meter 92 in other embodiments can, alternatively or additionally, incorporate other types of input and/or output devices, like speakers, lights, keypads, and microphones, to name a few examples. Moreover, the meter 92 can be configured to connect to other devices, such as computers, via a wired or wireless connection.

To index the tape in the cartridge 60, the meter includes an indexing mechanism 100 that engages the socket 80 in the reel 78 of the cartridge 60. In the illustrated embodiment, the indexing mechanism 100 includes a rotatable knob 102 that rotates a drive shaft 104, which in turn engages the socket 80 in the reel 78. The user indexes the tape 19 in the cartridge 60 by manually rotating the knob 102, but in other embodiments, a motor can be used to automatically index the tape 19. The indexing mechanism 100 can further incorporate a ratchet type mechanism to prevent the indexing mechanism 100 from operating backwards, thereby reducing the chance of reintroducing a contaminated section of the tape 19 back into the supply compartment 62 of the cartridge 60. In another embodiment, the indexing mechanism 100 operates in a fashion similar to a camera in which the firing button can only be actuated when the LIT unit 20 is properly positioned over the sample opening 74 in the cartridge 60. After the lancet 30 is fired, the indexing mechanism 100 is used to move the now used LIT unit 20 into the waste compartment 64.

Looking at FIG. 4, the meter 92 includes a contact engagement member 106 that aligns with the contact opening 72 in the cartridge 60. The contact engagement member 106 has contacts 108 that engage the contacts 47 on the LIT unit 20, when positioned over the sample opening 74 in the cartridge 60 in order to collect fluid. In one form, the contacts 108 of the meter 92 are leaf spring type contacts, but the contacts 108 in other embodiments can have a different shape.

To use the meter 92, the user rotates the indexing knob 102 such that the tape 19 in the cartridge 60 moves an unused LIT unit 20 into position over sample opening 74 in the cartridge 60, and once moved into position, the contacts 108 of the meter 92 engage the contacts 47 of the unused LIT unit 20. The tape 19 can be indexed before or after the user places the meter system 90 against the skin or other tissue to be lanced. To minimize the risk of contamination or infection, the user typically indexes the tape 19 after the test has been performed so that the used/contaminated LIT unit 20 is stored in the waste compartment 64. Once the system 90 is placed against the incision site (or in close proximity to the site), the user presses the firing button 98, which causes the lancet 30 (FIG. 1) to fire into the tissue and subsequently retract to form an incision in the tissue. Body fluid, such as blood and/or interstitial fluid, bleeds from the newly formed incision, and the body fluid is drawn into the capillary opening 49 of the capillary channel 48 via capillary action. The electronics in the meter 92 analyze the fluid sample in the capillary channel 48. As noted before, the electrodes in the channel 48 of the LIT unit 20 are coupled to the meter 92 via contacts 47. In the illustrated embodiment, the fluid sample is electrochemically analyzed, such as via amperometric, coulumetric, and/or potentiometric techniques, to name a few, but it should be understood that the fluid can be analyzed through other techniques, such as optically. The individual units 20 and/or the cartridge 60 can incorporate machine-readable coding, like barcodes, EEPROMS, resistance identification and the like, for calibrating the meter 92 and/or providing additional information. The results from the analysis are displayed on the display 94 of the meter 92 or outputted in some other manner. Once the sample is analyzed, the user can index the tape 19 via the indexing mechanism 100 so that the spent unit 20 is deposited in the waste compartment 64. Once all or nearly all of the units 20 are used, the user can dispose of the cartridge 60 and replace the cartridge 60 with a new one.

Figure 5:
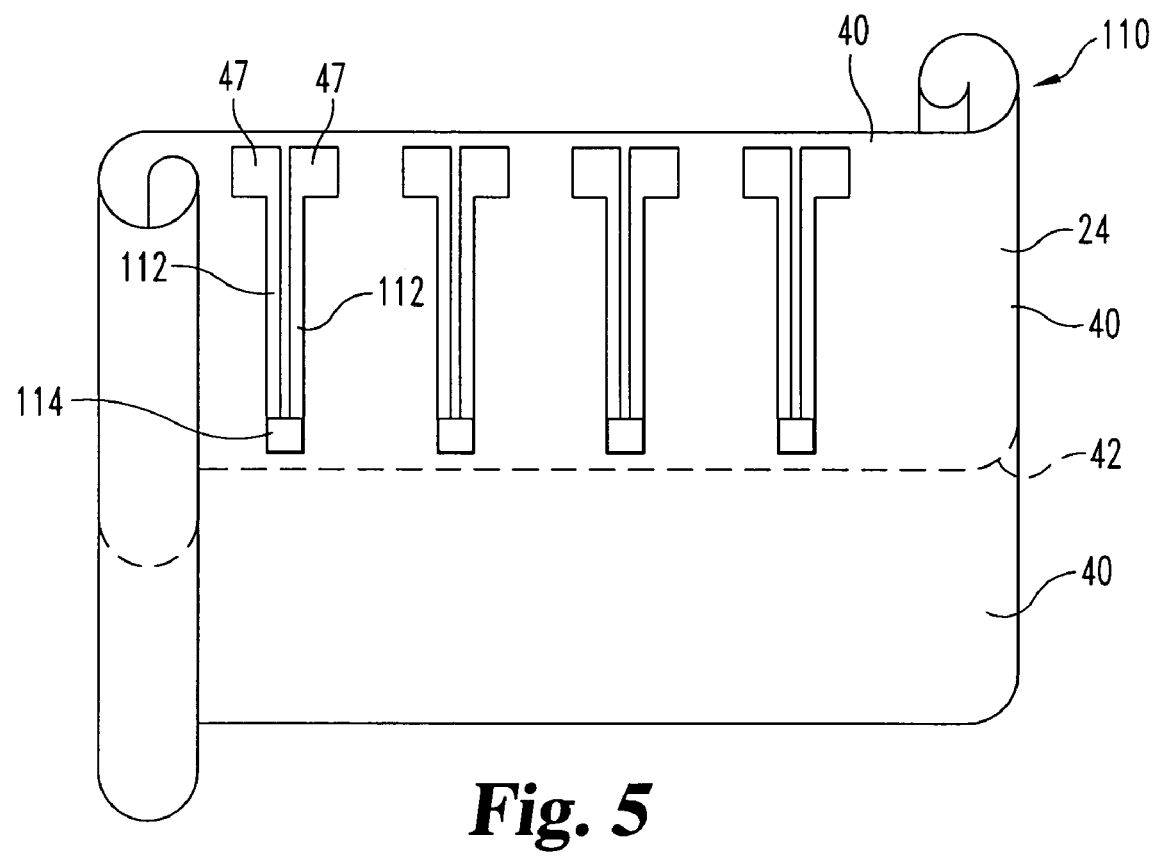
FIG. 5 is a first front view showing electrodes for a lancet integrated test element tape according to another embodiment.

An integrated test element tape 110 according to another embodiment will now be described with references to FIGS. 5 and 6. The illustrated test element tape 110 shares a number of features in common with the previously described embodiments, and for the sake of clarity as well as brevity, these common features will not be described in great detail below, but reference is made to the previous discussion. In the illustrated embodiment, the sterility sheet 24 acts as a base upon which the rest of test elements (strips) 111 are formed. Turning to FIG. 5, one or more electrodes 112 with contacts 47 are formed on the sterility sheet 24. The electrodes 112 can include electrodes of the type known to those skilled in the art, such as working, counter, and/or reference electrodes. It should be understood that the tape 110 can include more or less electrodes than are shown in the drawings. Moreover, it is contemplated that one of the electrodes 112 can be formed on the sterility sheet 24, while other electrodes 112 are formed on other layers of the test element 111. As can be seen, the analysis ends of the electrodes 112 (as well as the sterility sheet 24) are covered with a reagent 114 for analyzing the fluid sample. As should be appreciated, the reagent 114 includes chemicals for analyzing fluids, such as enzymes, mediators and the like, for example. It is envisioned that the reagent 114 can be applied to the sterility sheet 24 before or after the electrodes 112 are formed on the sterility sheet 24. Moreover, in other embodiments, the reagent 114 can be applied to other layers of the tape 110.

Figure 6:
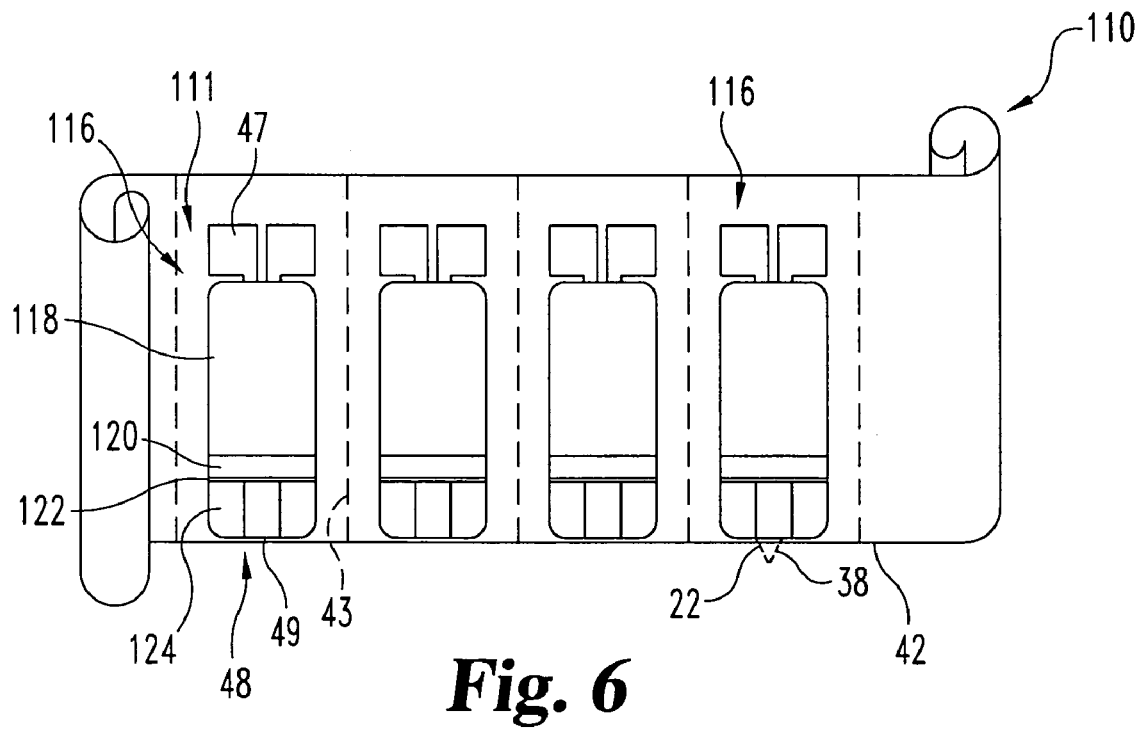
FIG. 6 is a second front view of the FIG. 5 test element tape once assembled.

Referring to FIG. 6, each LIT unit 116 includes a spacer member 118 that in part defines the capillary channel 48, and a vent member 120 that forms a vent slot 122 for venting air from the capillary channel 48. A cover layer or sheet 124 covers the capillary channel 48 in a manner such that the channel opening 49 is able to collect a fluid sample. Similar to the previous embodiments, the lancet 22 is enclosed in the sterility sheet 24 by folding the flaps 40 of the sheet 24 along fold line 42 and sealing the flaps 40 together. In FIG. 6, one of the LIT units 116 is shown with the tip 38 of the lancet 22 in an extended state in order to show how the tip 38 extends to puncture the sterility sheet 24, but it should be understood that the tip 38 is normally retracted inside the sheet 24 prior to use. Like the previous embodiments, the tape 110 is folded along fold lines 43 for packaging the tape in the supply compartment of a cartridge. As noted previously, the tape 110 at the fold lines 43 in one embodiment can be scored, perforated, or otherwise structured to promote folding, but in other embodiments, the fold lines 43 can be no different from the rest of the tape 110 and merely demark where the tape 110 is folded.

The tape 110 can by manufactured and sterilized via a number of techniques. As should be recognized, the lancet 22 can be sterilized utilizing any number of sterilization techniques. Moreover, the lancet 22 can be sterilized before being enclosed in the sterility sheet 24, or afterwards, such as through radiation sterilization. Some sterilization techniques are detrimental to the chemistry of reagents. A number of manufacturing techniques can be used to address this issue. In one embodiment, the lancet 22 is sterilized and enclosed within the sterility sheet 24 before the electrodes 112, the reagent 114, and other components of the LIT units 116 are applied to the sterility sheet 24. This technique reduces the chance of the chemistry in the reagent 114 being affected by the sterilization of the lancet 22. In another embodiment, some or all of components for the LIT units 116, which are not affected by the sterilization of the lancet 22, are attached prior to sterilization of the lancet 22. For instance, in one technique, the electrodes 112 are formed on the sterility sheet 24 before the lancet 22 is sterilized and enclosed in the sterility sheet 24. With another technique, the electrodes 112, spacer 118, and vent member 120 are attached to the sterility sheet 24 prior to the sterilization and enclosure of the lancet 22. After sterilization, the reagent 114 is deposited into the capillary channel 48 on or near the electrodes 112, and the cover sheet 124 is then applied over the capillary channel 48. In still yet another embodiment, all of the components of the test element, including the reagent 114, are assembled on the sterility sheet 24. Afterwards, the lancets 22 are sterilized and packaged in the sterility sheet 24 (or vice versa). In order to compensate for the affects of sterilization, the lot calibration readings, which are used to calibrate a meter prior to testing, are taken after the assembled units 116 have been sterilized.

Figure 7:
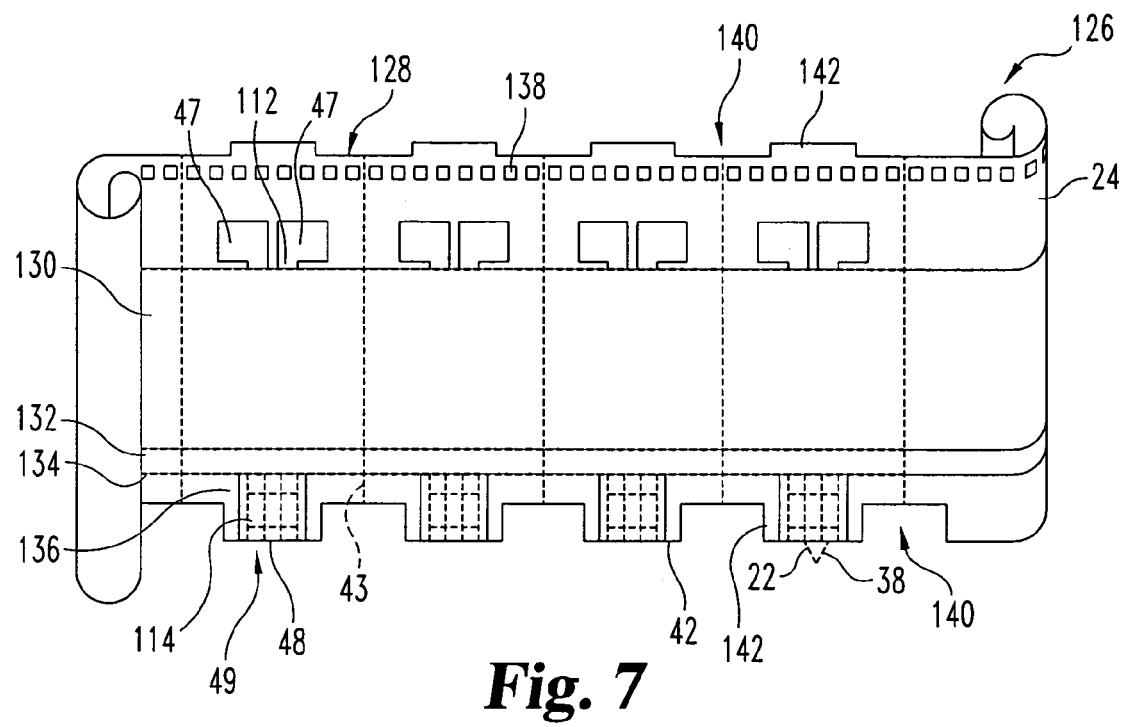
FIG. 7 is a front view of a lancet integrated test element tape according to a further embodiment.

A test element tape 126 with individual LIT units 128 according to another embodiment will be described with reference to FIGS. 7 and 8. The tape 126 in FIG. 7 is structurally similar to and shares a number of components in common with the tape 110 illustrated in FIGS. 5 and 6, and the tape 126 in FIG. 7 is likewise manufactured in a similar fashion to the one illustrated in FIGS. 5 and 6. For instance, the tape includes electrodes 112 formed on the sterility sheet 24, the reagent 114 for analyzing the fluid sample, and the lancet 22 wrapped in the sterility sheet 24. In the FIG. 7 embodiment, however, the individual units 128 are not separate and distinct, but rather, are formed from continuous layers of material. As shown, the tape 126 has a spacer layer 130 that in part defines the capillary channel 48 for each LIT unit 128, and a vent layer 132 that forms a vent slot 134 for venting air from the capillary channel 48. A cover layer or sheet 136 covers the capillary channel 48 in a manner such that the channel opening 49 is able to collect a fluid sample via capillary action. As shown, fold lines 43 are formed on the various layers between the individual units 128. The sterility sheet 24 further includes tractor holes 138 for a tractor feed mechanism that is used to index the tape 126. In the depicted embodiment, the tractor holes 138 are formed along one edge of the tape 126, but it should be appreciated that the tractor holes 138 can be located elsewhere, formed in other layers of the tape 126, and/or include multiple tractor hole rows. Moreover, it is contemplated that the tape 126 can be indexed in other manners. To orient and align the LIT units 128, alignment notches 140 are punched (or formed in some other manner) along the edges of the tape 126 to create alignment members 142, which act like alignment pins during folding and/or unfolding of the tape 126.

Figure 8:
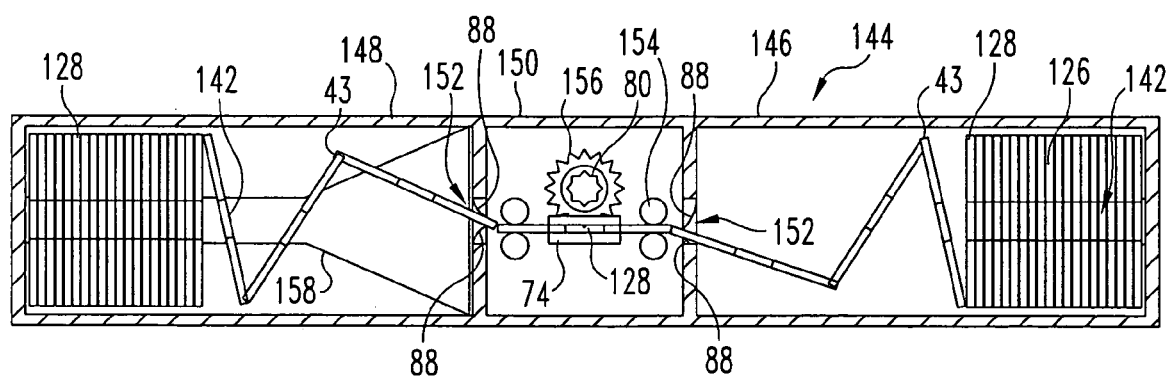
FIG. 8 is a cross sectional view of a cartridge according to still yet another embodiment.

A cartridge 144 in which the test element tape 126 is housed illustrated in FIG. 8. As shown, the cartridge 144 includes a supply compartment 146 in which the unused section of the tape 126 is stored and a waste compartment 148 in which the used section of the tape 126 is housed. Between the compartments 146, 148, the cartridge 144 has a sampling section 150 where the LIT units 128 collect and analyze fluid samples. Each compartment 146, 148 has an access opening 152 that faces the sampling section 150, which is sealed by seals 88. The sampling section 150 has a sample opening 74 through which the lancet 22 lances the tissue and the unit 128 draws the fluid into the sample chamber 48. In the illustrated embodiment, the sampling section 150 includes guides 154 for guiding the tape 126 and an indexing or feed mechanism 156 configured to engage the tractor holes 138 in order to index the tape 126. In the depicted embodiment, the feed mechanism 156 includes a tractor feed mechanism, but the feed mechanism 156 can includes other types of feed or indexing mechanisms. The feed mechanism 156 includes an engagement socket 80 where the meter engages and moves the feed mechanism 156. In the illustrated embodiment, the feed mechanism 156 includes a tractor gear. As should be recognized, the tape 126 can be guided and indexed in other manners. For instance, instead of the cartridge 144, the meter in other embodiments can incorporate the guide rollers 154 in the feed mechanism 156. In a further example, a tractor belt or other type of indexing structure can be used in place of the tractor gear. It is contemplated that the feed mechanism 156 can incorporate a ratchet or other similar type mechanism for preventing the feed mechanism 156 from operating in reverse. Moreover, the feed mechanism 156 can incorporate contacts for the meter that engage the contacts 47 on the tape 126.

In the FIG. 8 cartridge 144, the tape 126 is stored in a folded manner in both the supply 146 and waste 148 compartments, and both of the compartments 146, 148 are oriented in a longitudinal manner. With the tape 126 folded in both compartments 146, 148, the cartridge 144 has a generally compact configuration. During indexing, the feed mechanism 156 pulls on the tape 126 so as to unfold the tape 126 in the supply compartment 146. In the waste compartment 148, the tape 126 is folded along the fold lines 43 in a manner similar to a retractable wall or a folding closet door. Along both edges of the tape 126, the waste compartment 148 has guide channels 158 in which the alignment members 142 of the tape 126 are received. As the tape 126 is advanced by the feed mechanism 156, the guide channel 158 orients the tape 126 as the tape 126 folds. Within the sampling portion 150 of the cartridge 144, the alignment members 142 can also be used to sense the position of and/or orient each unit 128 over the sample opening 74. In addition to or as an alternative to the alignment members 142, it is envisioned that the tip 38 of the lancet 22 can remain slightly extended from the tape 126 so that the lancet 22 can be received in the guide channel 158 of the waste compartment 148 in order to align and/or guide the movement of the tape 126. In the depicted embodiment, the guide channel 158 is funnel shaped, but the guide channel 158 can have a different shape in other embodiments. It is contemplated that both compartments 146, 148 can have guide channels 158 in order to align the tape 126. Moreover, the compartments 146, 148 can have the guide channels 158 on a single wall of the compartment or on two opposing walls (or even more walls). Alternatively or additionally, one or more guide channels 158 can extend through the sampling section 150 of the cartridge 144 in order to guide the movement of the tape 126.

Figure 9:
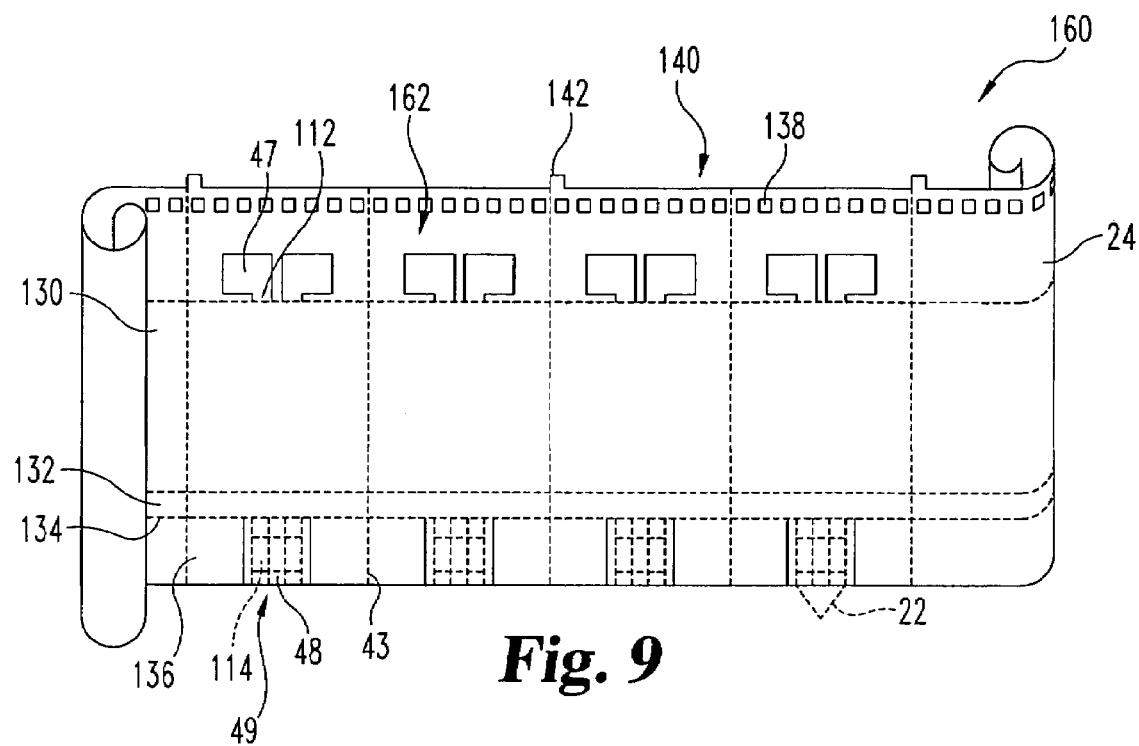
FIG. 9 is a front view of a lancet integrated test element tape according to another embodiment.

A variation of the FIG. 7 tape 126 is illustrated with tape 160 in FIG. 9. As can be seen, the tape 160 in FIG. 9 shares components in common with and is configured generally in the same fashion as the tape 126 of FIG. 7. Like before, the test element tape 160 in FIG. 9 includes the lancets 22, the sterility sheet 24, the capillary channels 48 with openings 49, electrodes 112 with contacts 47, the spacer layer 130, the vent layer 132 that forms the vent slot 134, the cover layer 136, and the tractor holes 138. For the sake of clarity and brevity, only the notable distinctions will be discussed below. Looking at FIG. 9, the test element tape 160 has the alignment notches 140 formed along only one edge of the tape 160 to form the alignment members 142. The alignment members 142 are formed on every other unit 162, near the fold line. It is contemplated that the alignment members 142 can be formed elsewhere on the tape 160.

Figure 10:
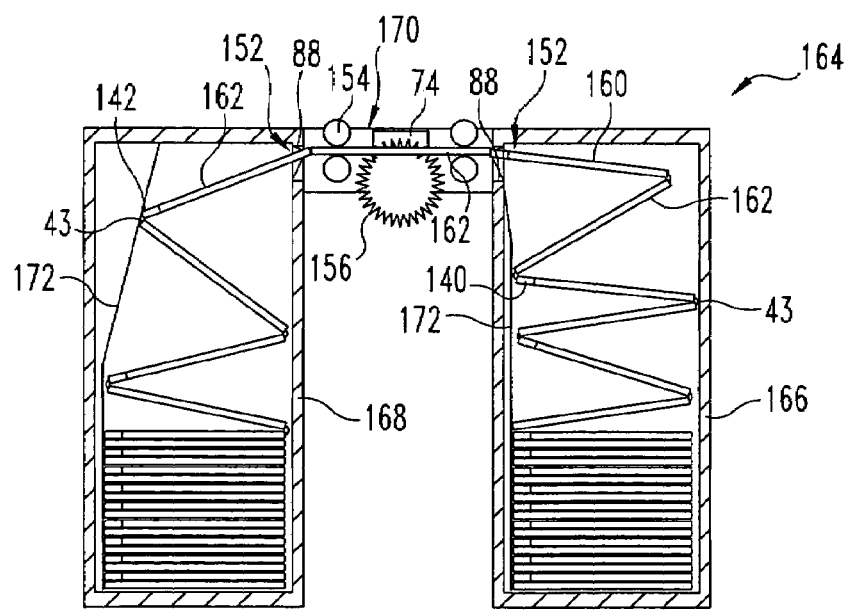
FIG. 10 is a cross sectional view of a cartridge according to still yet a further embodiment.

FIG. 10 illustrates a cartridge 164 configured to store and dispense the tape 160. In the FIG. 10 embodiment, supply 166 and waste 168 compartments are oriented in a side-by-side manner to give the cartridge 164 a compact, u-shaped profile. Nevertheless, the cartridges in other embodiments can be shaped differently. For instance, the cartridges in other embodiments can have a z-shaped profile or a circular shape, to name a few examples. In the circular shaped cartridge, the supply and waste compartment can be separated by a fixed wall or a sliding wall that allows the size of the compartments to change as the tape is used; that is, the supply compartment shrinks and the waste compartment grows as the tape is indexed into the waste compartment. Returning to the embodiment in FIG. 10, the tape 160 is stored in a folded manner in both the supply 166 and waste 168 compartments. The compartments 166, 168 each have access openings 152 with seals 88 for minimizing the risk of contamination.

A sampling portion 170 extends between the supply 166 and waste 168 compartments. In one form, the sampling portion 170 is integrated into the cartridge 164, and in other forms, the sampling portion 170 is separate from the cartridge 164 (e.g., incorporated into the meter and/or elsewhere). In the depicted embodiment, the sampling portion 170 includes guides 154 for guiding the tape 160, the feed mechanism 156, and the sample opening 74 where the fluid sample is collected. The sampling portion 170 can be open to the outside environment, partially open, or fully closed to the outside environment. The tractor feed mechanism 156 indexes the tape 160 by engaging the tractor holes 138 in the manner as previously described. It should be recognized that the tape can be indexed in other manners, and the feed mechanism 156 can be located elsewhere, such as in one of the compartments 166, 168 or on the meter, to name just a few examples. To guide the tape 160 as the tape 160 unfolds and folds, the compartments 166, 168 in the illustrated embodiment include one or more guide surfaces 172 that are configured to guide the alignment members 142 on the tape 160. As should be appreciated, the tape 160 can be unguided or guided in other manners as the tape 160 folds and unfolds.

A tape system according to yet another embodiment will be initially described with reference to FIGS. 11 and 12. In the illustrated embodiment, the system includes a test element tape 174 (FIG. 11) and a piercing member or lancet tape 176 (FIG. 12) that are originally separate from one another until after sterilization so as to avoid the unwanted affects of sterilization of the lancet tape 176 on the chemistry of the test element tape 174, which can affect calibration. With the tapes 174, 176 being separate, the problem of cross-contamination between the lancets and test elements is reduced.

Figure 11:
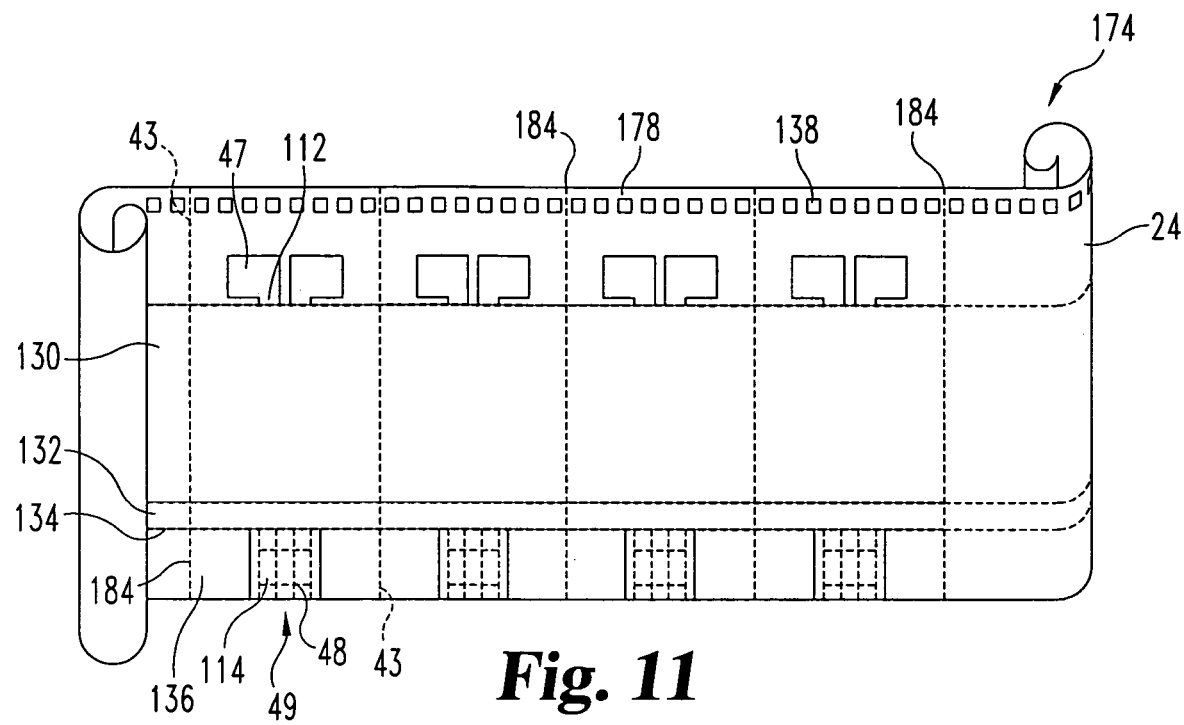
FIG. 11 is a front view of a test element tape according to another embodiment.

Looking at FIG. 11, the test element tape 174 includes a plurality of test elements 178 that are joined together on sheet 24 to form a continuous strip. Like the previous embodiments, each test element 178 includes electrodes 112 with contacts 47, at least one capillary channel 48 with sample opening 49, and reagent 114. Like before, continuous layers on the tape 174 form various components of the test elements 178, such as the spacer layer 130, the vent layer 132 that forms the vent slot 134, the cover layer 136, and the tractor holes 138. Between each element 178, the tape 174 has folds line 43 where the test element tape 174 is folded.

Figure 12:
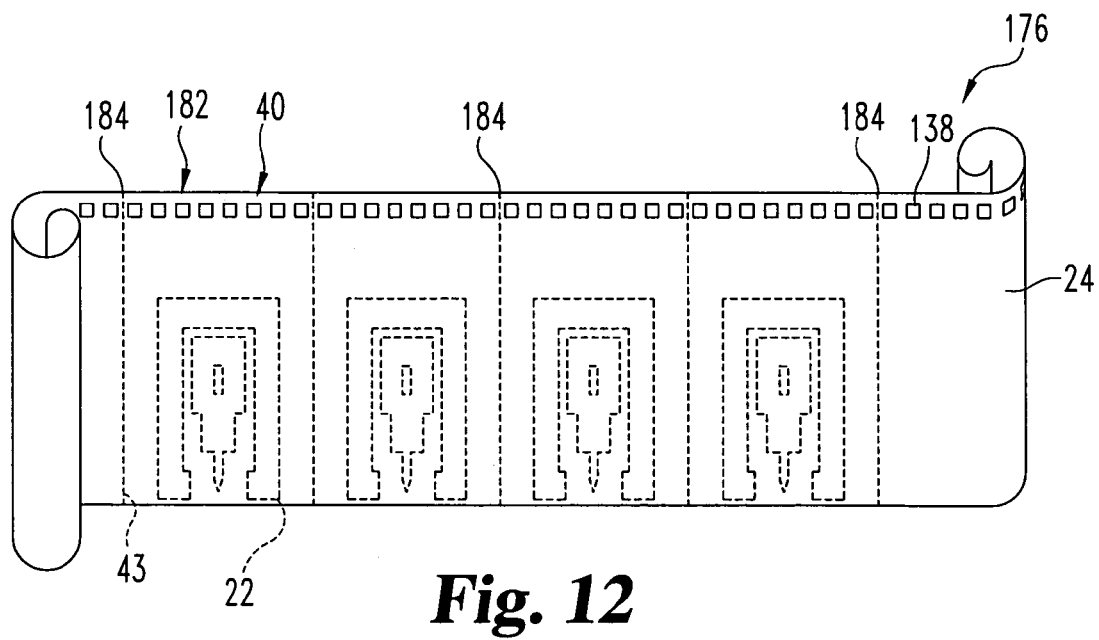
FIG. 12 is a front view of a lancet element tape configured for use in conjunction with the FIG. 11 test element tape.

With reference to FIG. 12, the lancet tape 176 include a plurality of incision forming members 22 that are wrapped in sterility sheet 24. In the illustrated embodiment, the incision forming members 22 include lancets, but it should be understood that other types of incision forming devices can be used. The incision forming members 22 in one form are sandwiched between folded flaps 40 of the sterility sheet 24. However, in other forms, the incision forming members 22 can be covered in other manners. To fold the lancet tape 176, fold lines 43 are defined between each lancet element 182. For indexing purposes, the lancet tape 176 in FIG. 12 has a series of tractor openings 138, but the lancet tape 176 can be indexed in other manners, which can make the tractor openings 138 optional, such as via a reel mechanism of the type illustrated in FIG. 3.

Figure 13:
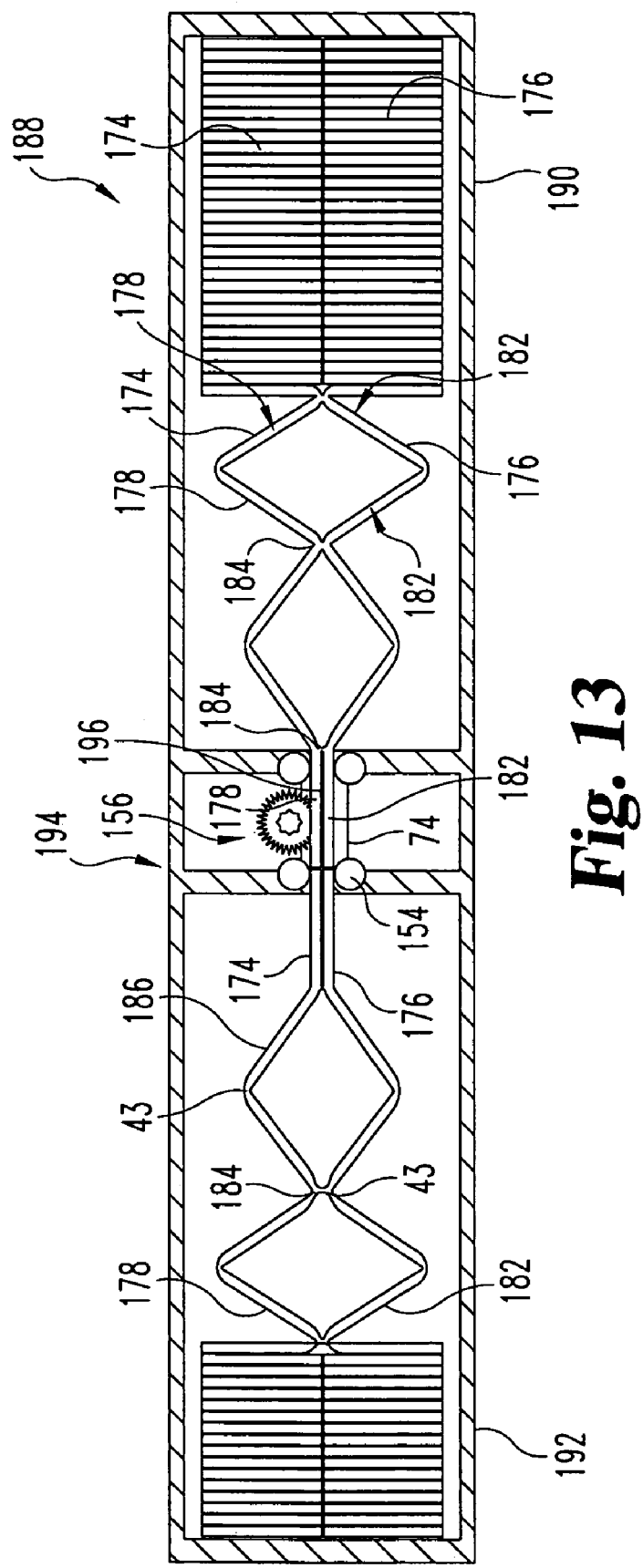
FIG. 13 is a cross sectional view of a cartridge according to a further embodiment.

For storage purposes, the tapes 174, 176 can be folded in a wide variety of fashions. FIG. 13 illustrates one manner in which the tapes 174, 176 can be folded. Referring to FIGS. 11, 12, and 13, the test element tape 174 and the lancet tape 176 are joined together at every other fold line 43, as indicated by reference numeral 184, to create a LIT tape 186. In other embodiments, the test element 174 and lancet 176 tapes can be joined together at other intervals, like at every third or fourth fold lines 43. Moreover, such intervals between join lines 184 can vary within a single LIT tape 186. In one embodiment, the tapes 174, 176 are joined together in a face-to-face manner in which the test elements 178 generally face the lancet tape 176, and in another embodiment, the test elements 178 face away from the lancet tape 176. In one form, when the test elements 178 face the lancet tape 176, the width of the lancet tape 176 is shorter such that the contacts 47 on the test element tape 174 remain exposed for contact with the meter.

FIG. 13 shows a cross-sectional view of a cartridge 188 in which the LIT tape 186 is housed. Like the previous embodiments, the cartridge 188 includes supply 190 and waste 192 compartments in which respectively unused and used sections of the LIT tape 186 are stored. In addition, the cartridge 188 includes a sampling portion 194 where a fluid sample is collected and analyzed. The sampling portion 194 includes feed mechanism 156 for feeding the LIT tape 186, one or more guides 154 that guide the LIT tape 186, and the sample opening 74 through which the sample is drawn.

In the supply compartment 190, the test elements 178 and the lancet elements 182 are packed in a stacked configuration. In other words, the test elements 178 in the test element tape 174 are folded upon one another, and the lancet elements 182 in the lancet tape 176 are folded upon one another. This results in the folded sections of the test element 174 and the lancet 176 tapes being positioned in a side-by-side fashion. As the feed mechanism 156 indexes the LIT tape 186, the LIT tape 186 unfolds in an accordion fashion. Once the LIT tape reaches the sampling portion 194, opposing guides 154 straighten the LIT tape 186 such that test element 174 and lancet 176 tapes are sandwiched together. Consequently, the test 178 and lancet 182 elements are brought together to create a LIT unit 196, at least on temporary basis. In the illustrated embodiment, opposing guides 154 squeeze the tapes 174, 176 together, but in other embodiments, other mechanisms can be used to press the tapes 174, 176 together. Once indexed over the sample opening 74, the lancet unit 182 of the LIT unit 196 can be used to form an incision from which a fluid sample is drawn and analyzed via the test element 178 of the LIT unit 196.

Afterwards, the now used LIT unit 196 is indexed into the waste compartment 192. In the waste compartment 192, the test element 174 and lancet element 176 tapes spread apart in an accordion fashion until the LIT tape 186 is folded in a stacked fashion like in the supply compartment 190. With such a construction, the packing density of the LIT tape 186 is enhanced such that the length of the supply 190 and waste 192 compartments can be shortened. Moreover, the risk of cross contamination between the test elements 178 and the lancet elements 182 before use is reduced because the test elements 178 and lancet elements 182 remain generally apart prior to use and only come into full contact just before use.

Figure 14:
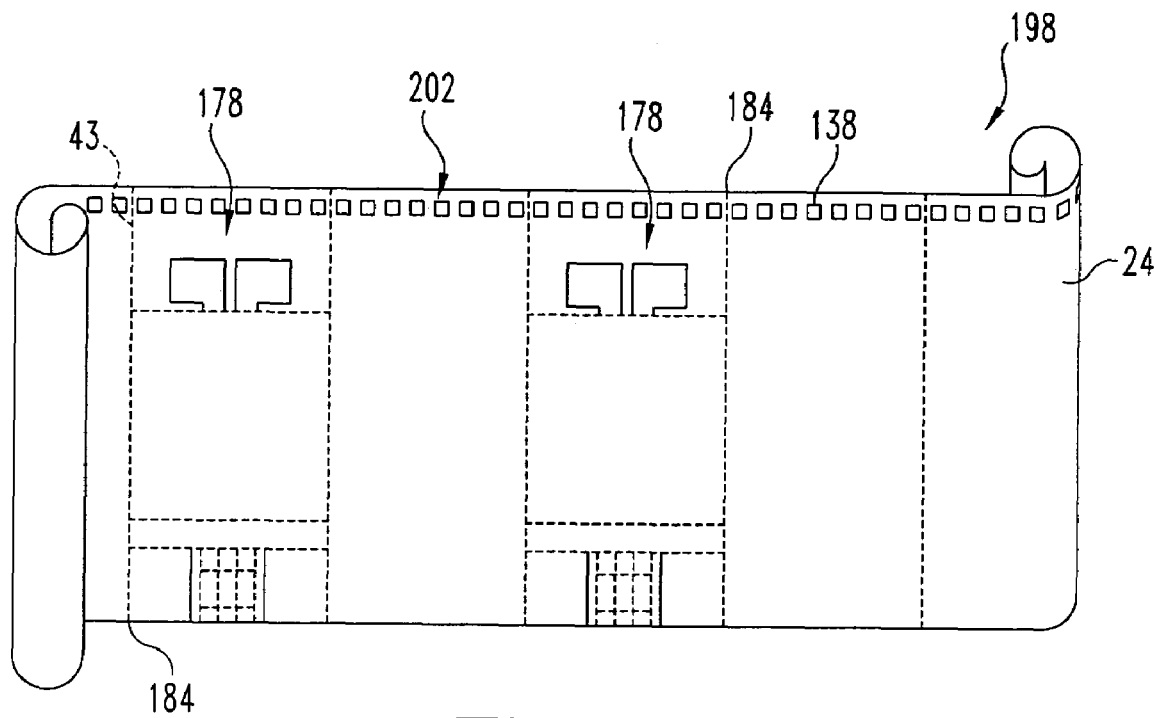
FIG. 14 is a front view of a test element tape according to another embodiment.
Figure 15:
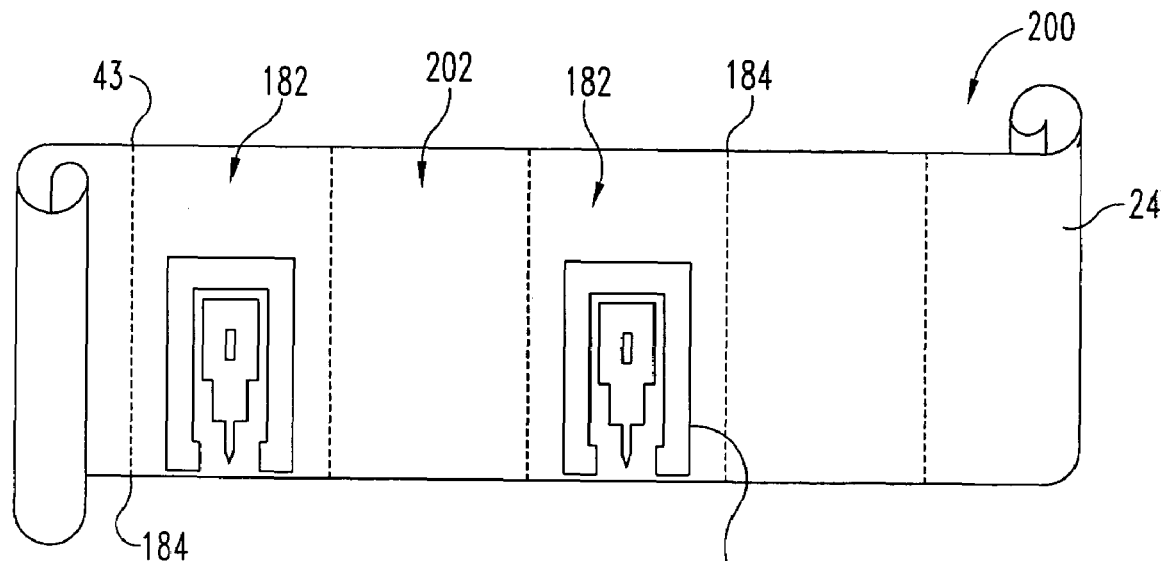
FIG. 15 is a front view of a lancet element tape configured for use in conjunction with the FIG. 14 test element tape.

A variation of a test element tape 198 and lancet tape 200 that can be used in the cartridge 188 of FIG. 13, as well as other types of cartridges, is illustrated in FIGS. 14 and 15. As can be seen, the test element tape 198 in FIG. 14 has the test elements 178 disposed on every other section of the sterility sheet 24, such that test elements 178 have blank or cover sections 202 in between the fold lines 43. Likewise, the lancet tape 200 in FIG. 15 has cover sections 202 in between the lancet elements 182. In the illustrated embodiment, only a single cover section 202 is located between the test 178 and lancet 182 elements, but in other embodiments, more than one cover section 202 can be located in between the elements 178, 182. The intervals of cover sections 202 can vary within the tape and/or vary from tape to tape. Moreover, the test tape 198 and the lancet tape 200 can have different intervals of cover sections 202. The cover sections 202 of the sterility sheet 24 fold over the test 178 and lancet 182 elements so as to protect and maintain the sterility of the elements 178, 182. As the tapes 198, 200 unfold, the cover sections 202 peel off the test 178 and lancet 182 elements, thereby exposing the test 178 and lancet 182 elements for testing purposes. For the FIG. 13 cartridge 188, the test 198 and lancet 200 tapes can be connected at join locations 184 or at other locations. In other embodiments, such as illustrated in FIG. 16, the test 198 and lancet 200 tapes can be disconnected before, during, and/or after collecting the fluid sample.

Figure 16:
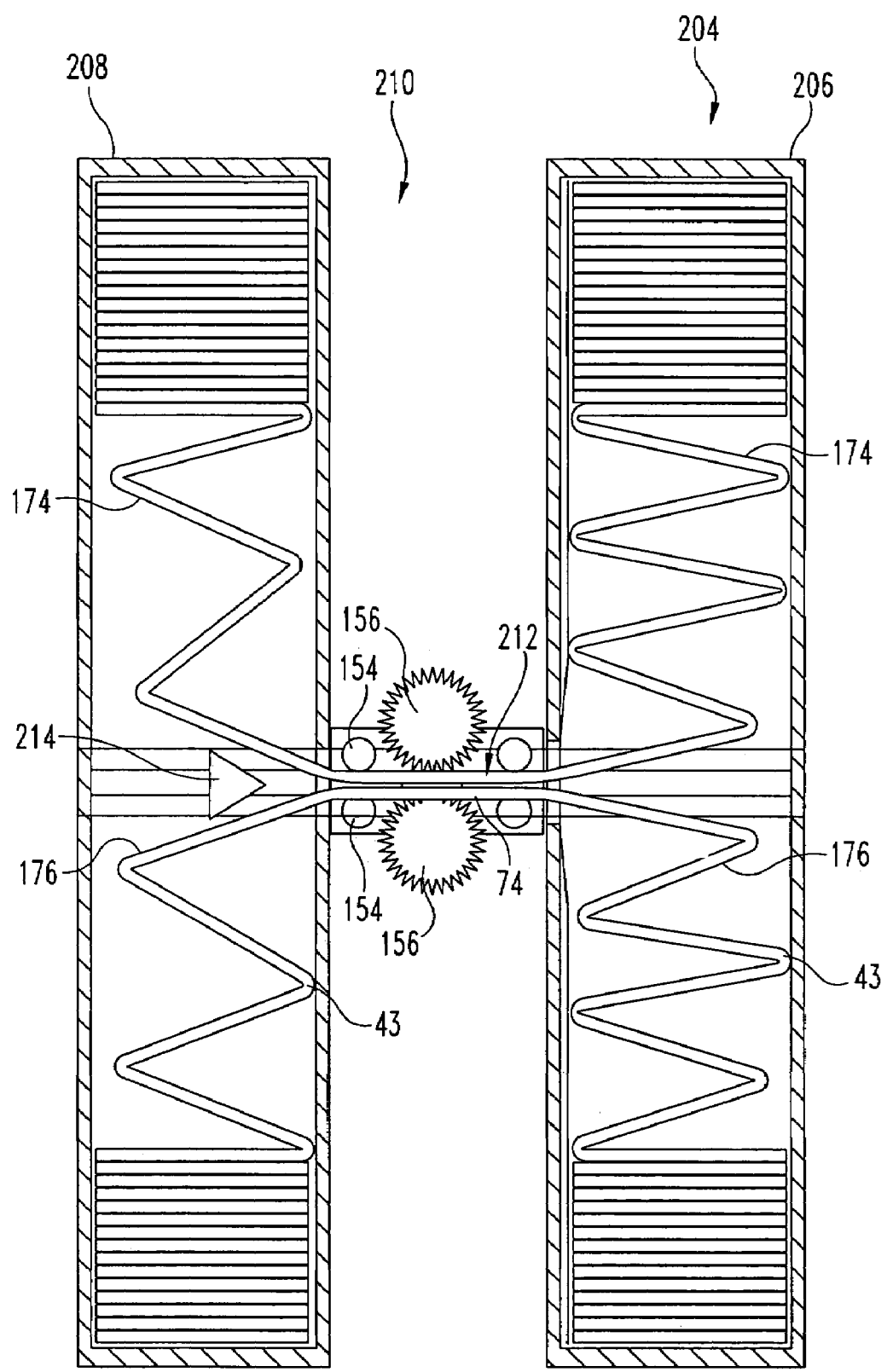
FIG. 16 is a cross sectional view of a cartridge according to still yet another embodiment.

FIG. 16 illustrates a LIT cartridge 204 according to another embodiment. In the illustrated embodiment, the cartridge 204 has a supply compartment 206 and a waste compartment 208 in which the test element tape 174 and the lancet tape 176 are stored separately. With the tapes 174, 176 separate, sterilization and calibration can be simplified along with the risk of cross contamination can be reduced. In other embodiments, the tapes 174, 176 can be connected together for storage purposes before or after use. It should be recognized that the cartridge 204 can house a variety of tapes, like the test element tape 198 of FIG. 14 and/or the lancet tape 200 of FIG. 15, to name a few examples. Between the supply 206 and waste 208 compartments, the cartridge 204 has a sampling portion 210 where the fluid sample is acquired and/or analyzed. In one embodiment, the sampling portion 210 includes one or more tape guides 154, one or more feed mechanisms 156, and the sampling opening 74 where the fluid is sampled. In the embodiment shown, the sampling portion 210 includes two pairs of guides 154 that position the tapes 174, 176 in close proximity to one another or in contact with one another so as to form, at least on a temporary basis, a LIT unit 212 for sampling and analyzing fluid samples. In one form, the tapes 174, 176 are pressed against another so that the test element 178 is able to collect fluid from the incision formed with the lancet element 182. In other forms, the tapes 174, 176 can be spaced slightly apart, but still in close proximity so that the test element 178 is still able to collect fluid. It should be understood that the sampling portion 210 can be configured differently in other embodiments. For example, the guides 154 can be optional in other embodiments and/or other types of feed mechanisms 156 can be used. The waste compartment 208 in the embodiment shown includes a separator member 214 that separates the tapes 174, 176 apart, but the separator member 214 can be optional in other embodiments.

From the previous discussion, it should be appreciated that the LIT units as well as the meters can be used to sample and analyze body fluid from various body parts like fingers and alternate sites, such as the forearm, for example. Moreover, the LIT units can be used to analyze numerous types of body fluids, such as interstitial fluid and blood, to name a few examples. The body fluid samples can be collected from body fluid bled onto the surface of the tissue or can be directly drawn from below the surface of the tissue. It also should be recognized that the features of the cartridges can be modified for use in other types of meters besides the one illustrated in the drawings. Conversely, the above-described meters can be used in conjunction with other types of cartridges. The cartridges and/or tapes can include machine readable coding that can provide a wide variety of information, such as lot coding and calibration information. For instance, the cartridges can include machine readable coding like barcodes, radio frequency identification (RFID) tags, magnetic encoding, electronic memory chips, and/or identification resistors, to name a few examples.

It is envisioned that that compartments in the cartridges can be integrated together to form a single unit or can be separate. Further, the waste and supply compartments in other embodiments can incorporate springs or other biasing members to bias the tapes. Moreover, the supply compartments can include desiccants for stabilizing the humidity of the supply compartments.

Regarding the tapes for the above-discussed embodiments, it is contemplated that a leader section can be incorporated into the tapes. It also should be appreciated that the tapes can be folded and/or oriented in other manners, besides in the manners as illustrated in the drawings. Furthermore, the LIT units in further embodiments can be configured in manners different from those shown in the drawings. For example, the lancet can be immovable or fixed relative to the test element. In another example, the lancet retracts via a rotational movement instead of linearly and/or the lancet extends at an angle relative to the opening of the capillary channel. It is contemplated that selected features from the various embodiments can be combined together in any number of other combinations. For instance, the waste compartment reel shown in FIG. 2 can be incorporated into the other illustrated embodiments in order to index the tape. Moreover, selected features can be adapted for other tapes that are used to collect and/or analyze body fluid samples, such as lancet tapes or test strip tapes.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents and patent applications cited in this specification are herein incorporated by reference as if each individual publication, patent or patent application was specifically and individually indicated to be incorporated by reference as set forth in its entirety herein.

What is claimed is:

1. An apparatus, comprising:
a lancet integrated test tape comprising a plurality of lancet integrated test units, the lancet integrated test units each comprising
a lancet configured to form an incision in tissue, and
a test element configured to analyze body fluid from the incision in the tissue; and
a cartridge comprising a supply compartment configured to store an unused section of the lancet integrated test tape, the lancet integrated test tape being folded within the supply compartment to limit damage to the lancet integrated test units;
wherein the lancet integrated test tape includes fold lines between each lancet integrated test unit;
wherein the lancets and test elements are joined together at alternating fold lines for folding the lancet integrated test tape in an accordion manner in which the lancets and test elements are folded away from each other within the supply compartment; and
wherein the lancet integrated test tape is configured to unfold during indexing in a manner in which the lancets and test elements are sandwiched together to form the lancet integrated test units.

2. The apparatus of claim 1, wherein the cartridge comprises a waste compartment in which a used section of the lancet integrated test tape is stored.

3. The apparatus of claim 2, wherein the waste compartment comprises a reel around which the used section of the lancet integrated test tape is wrapped.

4. The apparatus of claim 2, wherein the used section of the lancet integrated test tape is stored in a folded manner within the waste compartment.

5. The apparatus of claim 1, further comprising a feed mechanism configured to feed the lancet integrated test tape from the supply compartment.

6. The apparatus of claim 5, wherein the feed mechanism includes a reel configured to rotate to wrap the lancet integrated test tape around the reel.

7. The apparatus of claim 5, wherein:
the lancet integrated test tape has tractor openings; and
the feed mechanism includes a tractor mechanism that engages the tractor openings in the lancet integrated test tape.

8. The apparatus of claim 1, further comprising a meter coupled to the cartridge for providing analysis results from the test elements.

9. The apparatus of claim 1, wherein:
the lancets are incorporated into a lancet tape;
the test elements are incorporated into a test element tape; and
the lancet tape and test element tape are joined together at the alternating fold lines for folding the lancet integrated test tape in the accordion manner.

10. The apparatus of claim 1, wherein:
the lancet integrated test tape comprises cover sections between the lancet integrated test units that protect lancets and test elements prior to use; and
the cover sections are configured to peel away to expose the lancets and the test elements.

11. The apparatus of claim 4, in which the lancets and test elements are folded away from each other in the accordion manner within the waste compartment.

12. An apparatus, comprising:
A lancet integrated test tape comprising a plurality of lancet integrated test units created on a temporary basis, the lancet integrated test units each comprising
a lancet configured to form an incision in tissue, and
a test element configured to analyze body fluid from the incision in the tissue;
a cartridge comprising a supply compartment configured to store an unused section of the lancet integrated test tap, the lancet integrated test tape being folded within the supply compartment to limit damage to the lance integrated test units;
the lancets being incorporated into a lancet tape; the test elements being incorporated into a test element tape; and
wherein the lancet tape and the test element tap are folded and stored separately within the cartridge and brought together to temporarily create individual lancet integrated test units.

13. The apparatus of claim 12, further comprising:
one or more feed mechanisms to feed the lancet tape and the test element tape; and
one or more tape guides to guide the lancet tape and the test element tape together.

14. A lancet integrated test tape comprising a plurality of lancet integrated test units, the lancet integrated test units each comprising
a lancet configured to form an incision in tissue, and
a test element configured to analyze body fluid from the incision in the tissue;
a cartridge configured to store the lancet integrated test tap, the lancet integrated test tape being folded within the cartridge;
the cartridge including a guide channel; the lancet integrated test tape including one or more alignment members extending into the guide channel with the rest of the lancet integrated test tape extending outside of the guide channel, the lancet integrated test tape being configured to pivot about the one or more alignment members during folding and/or unfolding of the lancet integrated test tape; in which the one or more alignment members extend from at least one edge of the lancet integrated test tape.

15. The apparatus of claim 14, wherein the alignment members are defined by notches formed in the lancet integrated test tape.

16. The apparatus of claim 14, further comprising:
the cartridge including a waste compartment in which a used section of the lancet integrated test tape is stored, the waste compartment having the guide channel to guide folding of the lancet integrated test tape within the waste compartment.

* * * * *

UNITED STATES PATENT AND TRADEMARK OFFICE
CERTIFICATE OF CORRECTION

PATENT NO. : 7,481,777 B2  Page 1 of 1
APPLICATION NO. : 11/326422
DATED : January 27, 2009
INVENTOR(S) : Frank A. Chan It is certified that error appears in the above-identified patent and that said Letters Patent is hereby corrected as shown below:

Title Page; item (56);
Page 2, U.S. PATENT DOCUMENTS, replace --2006/0234388 A1 10/2006 Wong et al.-- with "2005/0234638 A1 10/2005 Wong et al."

Page 2, FOREIGN PATENT DOCUMENTS, replace --WO2005/04948 A1 11/2005-- with "WO2005/104948 A1 11/2005"

Col. 18, line 13, replace --store an unused section of the lancet integrated test tap-- with "store an unused section of the lancet integrated test tape"

Col. 18, line 35, replace --store an unused section of the lancet integrated test tap-- with "store an unused section of the lancet integrated test tape"

Signed and Sealed this

Twenty-fourth Day of March, 2009

JOHN DOLL
*Acting Director of the United States Patent and Trademark Office*